(12) United States Patent
Meltzer et al.

(10) Patent No.: US 6,353,105 B1
(45) Date of Patent: Mar. 5, 2002

(54) TROPANE ANALOGS AND METHODS FOR INHIBITION OF MONOAMINE TRANSPORT

(75) Inventors: Peter C. Meltzer, Lexington; Bertha K. Madras, Newton; Paul Blundell, Winchester; Zhengming Chen, Woburn, all of MA (US)

(73) Assignees: Organix, Inc., Woburn; President and Fellows of Harvard College, Cambridge, both of MA (US)

( * ) Notice: Subject to any disclaimer, the term of this patent is extended or adjusted under 35 U.S.C. 154(b) by 0 days.

(21) Appl. No.: 09/314,441

(22) Filed: May 19, 1999

Related U.S. Application Data

(62) Division of application No. 08/893,921, filed on Jul. 11, 1997, now Pat. No. 5,948,933, which is a continuation of application No. 08/552,584, filed on Nov. 5, 1995, now Pat. No. 6,171,576.

(51) Int. Cl.$^7$ .................. C07D 401/00; C07D 451/02
(52) U.S. Cl. ........................ 546/125; 546/127
(58) Field of Search ................... 546/125, 127

(56) References Cited

U.S. PATENT DOCUMENTS

| | | | |
|---|---|---|---|
| 3,813,404 A | 5/1974 | Clarke et al. | 260/292 |
| 5,276,211 A | 1/1994 | Narula et al. | 568/807 |
| 5,288,872 A | 2/1994 | Davies et al. | 546/132 |
| 5,310,912 A | 5/1994 | Neumeyer et al. | 546/132 |
| 5,374,636 A | 12/1994 | Moldt et al. | 514/304 |
| 5,736,123 A | 4/1998 | Carroll | 424/1.85 |
| 5,736,556 A | 4/1998 | Moldt et al. | 514/304 |

OTHER PUBLICATIONS

Blough et al., J. Med. Chem. 39:4027–4035 (1996).
Clarke, et al., J. Med. Chem. 16:1260–1267 (1973).
Davies, et al., J. Med. Chem. 39:2554–2558 (1996.
Holmquist, et al., J. Med. Chem. 39:4139–4141 (1996).
Kozikowski, et al., Tetrahedron Lett. 37:5333–5336 (1996).
Meltzer, et al., J. Med. Chem. 36:855–862 (1993).
Meltzer, et al., J. Med. Chem. 37:2001–2010 (1994).
Meltzer, et al., J. Med. Chem. 39:371–379 (1996).
Simoni, et al., J. Med. Chem. 36:3975–3977 (1993).
Meltzer, et al., J. Med. Chem. 40:2661–2673 (1997).

*Primary Examiner*—Joseph K. McKane
*Assistant Examiner*—T. A. Solola
(74) *Attorney, Agent, or Firm*—Dike, Bronstein, Roberts, Cushman IP Group of Edwards & Angell, LLP; George W. Neuner

(57) ABSTRACT

New tropane analogs that bind to monoamine transporters are described, particularly, 8-aza, 8carbo and 8-oxo tropanes having 6- or 7-substituents. The compounds of the present invention can be racemic, pure R-enantiomers, or pure S-enantiomers. Certain preferred compounds of the present invention have a high selectivity for the DAT versus the SERT. Also described are pharmaceutical therapeutic compositions comprising the compounds formulated in a pharmaceutically acceptable carrier and a method for inhibiting 5-hydroxy-tryptamine reuptake of a monoamine transporter by contacting the monoamine transporter with a 5-hydroxytryptamine reuptake inhibiting amount of a compound of the present invention. Preferred monoamine transporters for the practice of the present invention include the dopamine transporter, the serotonin transporter and the norepinephrine transporter.

36 Claims, 4 Drawing Sheets

Or 6-OX substituted compounds

Or 6-OX substituted compounds

| 47 | R |
|---|---|
| a | H |
| b | F |
| c | Cl (1R/1S) |
| d | 3,4-Cl₂ (1R/1S) |
| e | 3,4-Cl₂ (1R) |
| f | 3,4-Cl₂ (1S) |

TROPANE ANALOGS AND METHODS FOR INHIBITION OF MONOAMINE TRANSPORT

This application is a division of Ser. No. of 08/893,921 filed on Jul. 11, 1997, now U.S. Pat. No. 5,948,933, and is a continuation in part of Ser. No. 08/552,584 filed Nov. 3, 1995, now U.S. Pat. No. 6,171,576.

STATEMENT REGARDING FEDERALLY SPONSORED RESEARCH OR DEVELOPMENT

This invention was supported by NIH Grant Nos. DA48309, DA06303 and DA09462, and by Contract NO1DA 7-8081 and Grant RO1DA 11542, which are supported by the National Institute on Drug of Abuse (NIDA). The government has certain rights to the invention.

FIELD OF THE INVENTION

This invention relates to tropane analogs of cocaine and their use as inhibitors of monoamine reuptake.

BACKGROUND OF THE INVENTION

Cocaine dependence is a problem of national significance. To date no cocaine pharmacotherapy has been reported. Cocaine is a potent stimulant of the mammalian central nervous system. Its reinforcing properties and stimulant effects are associated with its propensity to bind to monoamine transporters, particularly the dopamine transporter (DAT). (Kennedy, L. T. and I. Hanbauer (1983), *J. Neurochem.* 34: 1137–1144; Kuhar, M. J., M. C. Ritz and J. W. Boja (1991), *Trends Neurosci.* 14: 299–302; Madras, B. K., M. A. Fahey, J. Bergman, D. R. Canfield and R. D. Spealman (1989), *J. Pharmacol. Exp. Ther.* 251: 131–141; Madras, B. K., J. B. Kamien, M. Fahey, D. Canfield, et al. (1990), *Pharmacol Biochem. Behav.* 35: 949–953; Reith, M. E. A., B. E. Meisler, H. Sershen and A. Lajtha (1986), *Biochem. Pharmacol.* 35: 1123–1129; Ritz, M. C., R. J. Lamb, S. R. Goldberg and M. J. Kuhar (1987), *Science* 237: 1219–1223; Schoemaker, H., C. Pimoule, S. Arbilla, B. Scatton, F. Javoy-Agid and S. Z. Langer (1985), *Naunyn-Schmiedeberg's Arch. Pharmacol.* 329: 227–235.) It also binds with substantial potency to serotonin transporters (SERT) and norepinephrine transporters.

Structure activity relationship (SAR) studies have largely focused on a series of cocaine analogs. Among the more potent of these congeners at $^3$H-cocaine binding sites in striatum (Madras, B. K., M. A. Fahey, J. Bergman, D. R. Canfield and R. D. Spealman (1989), *J. Pharmacol. Exp. Ther.* 251: 131–141; Reith, M. E. A., B. E. Meisler, H. Sershen and A. Lajtha (1986), *Biochem. Pharmacol.* 35: 1123–1129) is (1R)-3β-(4-fluorophenyl)tropane-2β-carboxylic acid methyl ester, (WIN35,428 or CFT) (Kaufman, M. J. and B. K. Madras (1992), *Synapse* 12: 99–111; Madras, B. K., M. A. Fahey, J. Bergman, D. R. Canfield and R. D. Spealman (1989), *J. Pharmacol. Exp. Ther.* 251: 131–141) reported in 1973 (Clarke, R. L., S. J. Daum, A. J. Gambino, M. D. Aceto, et al. (1973), *J. Med. Chem.* 16: 1260–1267). This compound was subsequently radiolabeled to provide a selective probe for the DAT in primate brain. (Canfield, D. R., R. D. Spealman, M. J. Kaufman and B. K. Madras (1990), *Synapse* 6: 189–195; Kaufman, M. J. and B. K. Madras (1991), *Synapse* 9: 43–49; Kaufman, M. J., R. D. Spealman and B. K. Madras (1991), *Synapse* 9: 177–187.)

Among the most potent tropane inhibitors of monoamine binding sites in striatum are 3β-{4-(1-methylethenyl)-phenyl}-2β-propanoyl-8-azabicyclo(3.2.1)octane and 3β-(2-naphthyl)-2β-propanoyl-8-azabicyclo(3.2.1)octane, (Bennett, B. A., C. H. Wichems, C. K. Hollingsworth, H. M. L. Davies, C. Thornley, T. Sexton and S. R. Childers (1995), *J. Pharm. Exp. Ther.* 272: 1176–1186; Davies, H. M. L., L. A. Kuhn, C. Thornley, J. J. Matasi, T. Sexton and S. R. Childers (1996), *J. Med. Chem.* 39: 2554–2558) (1R)-RTI55 (βCIT), (Boja 1991; Boja, J. W., A. Patel, F. I. Carroll, M. A. Rahman, et al. (1991), *Eur. J. Pharmacol.* 194: 133–134; Neumeyer, J. L., S. Wang, R. A. Milius, R. M. Baldwin, et al. (1991), *J. Med. Chem.* 34: 3144–3146) (1R)-RTI121, (Carroll, F. I., A. H. Lewin, J. W. Boja and M. J. Kuhar (1992), *J. Med. Chem.* 35: 969–981.) and (1R)-3β-(3,4-dichlorophenyl)-tropane-2β-carboxylic acid methyl ester (O-401), (Carroll, F. I., M. A. Kuzemko and Y. Gao (1992), *Med. Chem Res.* 1: 382–387; Meltzer, P. C., A. Y. Liang, A.-L. Brownell, D. R. Elmaleh and B. K. Madras (1993), *J. Med. Chem.* 36: 855–862).

SAR studies of the binding of these agents and their effects on monoamine transporter function have been reported. (Blough, B. E., P. Abraham, A. H. Lewin, M. J. Kuhar, J. W. Boja and F. I. Carroll (1996), *J. Med. Chem.* 39: 4027–4035; Carroll, F. I., P. Kotian, A. Dehghani, J. L. Gray, et al. (1995), *J. Med. Chem.* 38: 379–388; Carroll, F. I., A. H. Lewin, J. W. Boja and M. J. Kuhar (1992), y *J. Med. Chem.* 35: 969–981; Carroll, F. I., S. W. Mascarella, M. A. Kuzemko, Y. Gao, et al. (1994), *J. Med. Chem.* 37: 2865–2873; Chen, Z., S. Izenwasser, J. L. Katz, N. Zhu, C. L. Klein and M. L. Trudell (1996), *J. Med. Chem.* 39: 4744–4749; Davies, H. M. L., L. A. Kuhn, C. Thornley, J. J. Matasi, T. Sexton and S. R. Childers (1996), *J. Med. Chem.* 39: 2554–2558; Davies, H. M. L., Z.-Q. Peng and J. H. Houser (1994), *Tetrahedron Lett.* 48: 8939–8942; Davies, H. M. L., E. Saikali, T. Sexton and S. R. Childers (1993), *Eur. J. Pharmacol. Mol. Pharm.* 244: 93–97; Holmquist, C. R., K. I. Keverline-Frantz, P. Abraham, J. W. Boja, M. J. Kuhar and F. I. Carroll (1996), *J. Med. Chem* 39: 4139–4141; Kozikowski, A. P., G. L. Araldi and R. G. Ball (1997), *J. Org. Chem.* 62: 503–509; Kozikowski, A. P., M. Roberti, L. Xiang, J. S. Bergmann, P. M. Callahan, K. A. Cunningham and K. M. Johnson (1992), *J. Med. Chem.* 35: 4764–4766; Kozikowski, A. P., D. Simoni, S. Manfredini, M. Roberti and J. Stoelwinder (1996), *Tetrahedron Lett.* 37: 5333–5336; Meltzer, P. C., A. Y. Liang, A.-L. Brownell, D. R. Elmaleh and B. K. Madras (1993), *J. Med. Chem.* 36: 855–862; Meltzer, P. C., A. Y. Liang and B. K. Madras (1994), *J. Med. Chem.* 37: 2001–2010; Meltzer, P. C., A. Y. Liang and B. K. Madras (1996), *J. Med. Chem.* 39: 371–379; Newman, A. H., A. C. Allen, S. Izenwasser and J. L. Katz (1994), *J. Med Chem.* 37: 2258–2261; Newman, A. H., R. H. Kline, A. C. Allen, S. Izenwasser, C. George and J. L. Katz (1995), *J. Med. Chem.* 38: 3933–3940; Shreekrishna, V. K., S. Izenwasser, J. L. Katz, C. L. Klein, N. Zhu and M. L. Trudell (1994), *J. Med. Chem.* 37: 3875–3877; Simoni, D., J. Stoelwinder, A. P. Kozikowski, K. M. Johnson, J. S. Bergmann and R. G. Ball (1993), *J. Med. Chem.* 36: 3975–3977.)

Binding of cocaine and its tropane analogs to monoamine transporters is stereoselective. As example (1R)-(−)-cocaine binds at the dopamine transporter about 200-fold more potently than the unnatural isomer, (1S)-(+)-cocaine. (Kaufman, M. J. and B. K. Madras (1992), *Synapse* 12: 99–111; Madras, B. K., M. A. Fahey, J. Bergman, D. R. Canfield and R. D. Spealman (1989), *J. Pharmacol. Exp. Ther.* 251: 131–141; Madras, B. K., R. D. Spealman, M. A. Fahey, J. L. Neumeyer, J. K. Saha and R. A. Milius (1989), *Mol. Pharmacol.* 36: 518–524; Reith, M. E. A., B. E. Meisler, H. Sershen and A. Lajtha (1986), *Biochem. Phar-* macol. 35: 1123–1129; Ritz, M. C., R. J. Lamb, S. R. Goldberg and M. J. Kuhar (1987), *Science* 237: 1219–1223.)

Also, only the R-enantiomers of cocaine have been found active in a variety of biological and neurochemical measures. (Clarke, R. L., S. J. Daum, A. J. Gambino, M. D. Aceto, et al. (1973), *J. Med. Chem.* 16: 1260–1267; Kaufman, M. J. and B. K. Madras (1992), *Synapse* 12: 99–111; Madras, B. K., M. A. Fahey, J. Bergman, D. R. Canfield and R. D. Spealman (1989), *J. Pharmacol. Exp. Ther.* 251: 131–141; Madras, B. K., R. D. Spealman, M. A. Fahey, J. L. Neumeyer, J. K. Saha and R. A. Milius (1989), *Mol. Pharmacol.* 36: 518–524; Reith, M. E. A., B. E. Meisler, H. Sershen and A. Lajtha (1986), *Biochem. Pharmacol.* 35: 1123–1129; Ritz, M. C., R. J. Lamb, S. R. Goldberg and M. J. Kuhar (1987), *Science* 237: 1219–1223; Sershen, H., M. E. A. Reith and A. Lajtha (1980), *Neuropharmacology* 19: 1145–1148; Sershen, H., M. E. A. Reith and A. Lajtha (1982), *Neuropharmacology* 21: 469–474; Spealman, R. D., R. T. Kelleher and S. R. Goldberg (1983), *J. Pharmacol. Exp. Ther.* 225: 509–513.) Parallel stereoselective behavioral effects have also been observed. (Bergman, J., B. K. Madras, S. E. Johnson and R. D. Spealman (1989), *J. Pharmacol. Exp. Ther.* 251: 150–155; Heikkila, R. E., L. Manzino and F. S. Cabbat (1981), *Subst. Alcohol Actions/Misuse* 2: 115–121; Reith, M. E. A., B. E. Meisler, H. Sershen and A. Lajtha (1986), *Biochem. Pharmacol.* 35: 1123–1129; Spealman, R. D., R. T. Kelleher and S. R. Goldberg (1983), *J. Pharmacol. Exp. Ther.* 225: 509–513; Wang, S., Y. Gai, M. Laruelle, R. M. Baldwin, B. E. Scanlet, R. B. Innis and J. L. Neumeyer (1993), *J. Med. Chem.* 36: 1914–1917.) For example, in primates and rodents the stimulating and reinforcing properties of the (−)-enantiomer of cocaine or its 3-aryltropane analogs were considerably greater than for the (+)-enantiomers.

Although SAR studies of cocaine and its 3-aryltropane analogs have offered insight into their mode of binding to monoamine transporters, a comprehensive picture of the binding interaction at the molecular level has not emerged. SAR studies on the classical tropane analogs (Carroll, F. I., Y. Gao, M. A. Rahman, P. Abraham, et al. (1991), *J. Med. Chem.* 34: 2719–2725; Carroll, F. I., S. W. Mascarella, M. A. Kuzemko, Y. Gao, et al. (1994), *J. Med. Chem.* 37: 2865–2873; Madras, B. K., M. A. Fahey, J. Bergman, D. R. Canfield and R. D. Spealman (1989), *J. Pharmacol. Exp. Ther.* 251: 131–141; Madras, B. K., R. D. Spealman, M. A. Fahey, J. L. Neumeyer, J. K. Saha and R. A. Milius (1989), *Mol. Pharmacol.* 36: 518–524; Meltzer, P. C., A. Y. Liang, A.-L. Brownell, D. R. Elmaleh and B. K. Madras (1993), *J. Med. Chem.* 36: 855–862; Reith, M. E. A., B. E. Meisler, H. Sershen and A. Lajtha (1986), *Biochem. Pharmacol.* 35: 1123–1129) appeared to provide a consistent model for this interaction with the DAT, however, subsequent studies revealed inconsistencies. (Carroll, F. I., P. Kotian, A. Dehghani, J. L. Gray, et al. (1995), *J. Med. Chem.* 38: 379–388; Chen, Z., S. Izenwasser, J. L. Katz, N. Zhu, C. L. Klein and M. L. Trudell (1996), *J. Med. Chem.* 39: 4744–4749; Davies, H. M. L., L. A. Kuhn, C. Thornley, J. J. Matasi, T. Sexton and S. R. Childers (1996), *J. Med. Chem.* 39: 2554–2558; Kozikowski, A. P., G. L. Araldi and R. G. Ball (1997), *J. Org. Chem.* 62: 503–509; Meltzer, P. C., A. Y. Liang and B. K. Madras (1994), *J. Med. Chem.* 37: 2001–2010; Meltzer, P. C., A. Y. Liang and B. K. Madras (1996), *J. Med. Chem.* 39: 371–379.)

Carroll had proposed (Boja, J. W., R. M. McNeill, A. Lewin, P. Abraham, F. I. Carroll and M. J. Kuhar (1992), *Mol. Neurosci.* 3: 984–986; Carroll, F. I., P. Abraham, A. Lewin, K. A. Parham, J. W. Boja and M. J. Kuhar (1992), *J. Med. Chem.* 35: 2497–2500; Carroll, F. I., Y. Gao, M. A. Rahman, P. Abraham, et al. (1991), *J. Med. Chem.* 34: 2719–2725; Carroll, F. I., M. A. Kuzemko and Y. Gao (1992), *Med. Chem Res.* 1: 382–387) four molecular requirements for binding of cocaine and its tropane analogs at the DAT: a 2β-carboxy ester, a basic nitrogen capable of protonation at physiological pH, the R-configuration of the tropane and a 3β-aromatic ring at $C_3$. However, Davies (Davies, H. M. L., E. Saikali, T. Sexton and S. R. Childers (1993), *Eur. J. Pharmacol. Mol. Pharm.* 244: 93–97) later reported that introduction of 2β-ketones did not reduce potency. Kozikowski questioned the role of hydrogen bonding at the $C_2$ site because introduction of unsaturated and saturated alkyl groups (Kozikowski, A. P., M. Roberti, K. M. Johnson, J. S. Bergmann and R. G. Ball (1993), *Bioorg. Med. Chem. Lett.* 3: 1327–1332; Kozikowski, A. P., M. Roberti, L. Xiang, J. S. Bergmann, P. M. Callahan, K. A. Cunningham and K. M. Johnson (1992), *J. Med. Chem.* 35: 4764–4766) did not diminish binding. Further, the ionic bond between a protonated amine (at physiologically pH) and the presumed (Kitayama, S., S. Shimada, H. Xu, L. Markham, D. H. Donovan and G. R. Uhl (1993), *Proc. Natl. Acad. Sci. U.S.A.* 89: 7782–7785) aspartate residue on the DAT was questioned because reduction of nitrogen nucleophilicity (Kozikowski, A. P., M. K. E. Saiah, J. S. Bergmann and K. M. Johnson (1994), *J. Med. Chem.* 37(37): 3440–3442) by introduction of N-sulfones did not reduce binding potency.

It also has been reported (Madras, B. K., J. B. Kamien, M. Fahey, D. Canfield, et al. (1990), *Pharmacol Biochem. Behav.* 35: 949–953) that introduction of an alkyl or allyl group did not eliminate binding potency. An N-iodoallyl group on the tropane has provided potent and selective ligands for the DAT, and altropane is currently being developed as a SPECT imaging agent (Elmaleh, D. R., B. K. Madras, T. M. Shoup, C. Byon, et al. (1995), *J. Nucl. Chem.*, 37 1197–1202 (1966); Fischman, A. J., A. A. Bonab, J. W. Babich, N. M. Alpert, et al. (1996), *Neuroscience-Net* 1, 00010, (1997). A $^{99m}$technetium labeled compound, technepine, which binds potently and selectively to the DAT and provides excellent in vivo SPECT images has been reported. (Madras, B. K., A. G. Jones, A. Mahmood, R. E. Zimmerman, et al. (1996), *Synapse* 22: 239–246.) (Meltzer, P. C., Blundell, P., Jones, A. G., Mahmood, A., Garada, B. et al., *J. Med. Chem.*, 40, 1835–1844, (1997). 2-Carbomethoxy-3-(bis(4-fluorophenyl)methoxy)tropanes have been reported (Meltzer, P. C., A. Y. Liang and B. K. Madras (1994), *J. Med. Chem.* 37: 2001–2010). The S-enantiomer, (S)-(+)-2β-carbomethoxy-3α-(bis(4-fluorophenyl)methoxy)tropane (Difluoropine) was considerably more potent ($IC_{50}$: 10.9 nM) and selective (DAT v. SERT: 324) than any of the other seven isomers, including the R-enantiomers.

Drug therapies for cocaine abuse are needed. Also, there is a need for protective agents for neurodegenerative diseases such as Parkinson's disease and Alzheimer's disease as well as therapeutic agents for dopamine related dysfunction such as Attention Deficit Disorder. Compounds that inhibit monoamine reuptake in the mammalian system are sought to provide such therapies.

Inhibition of 5-hydroxytryptamine reuptake has an effect on diseases mediated by 5HT receptors. Compounds that provide such inhibition can be useful, for example, as therapeutic anti-depressants.

Cocaine recognition sites are localized on monoamine transporters such as, for example, the dopamine transporter (DAT) and serotonin transporter (SERT). These transporters are localized, in turn, on monoamine nerve terminals. Compounds that bind to these sites can be useful as (i) probes for neuro-degenerative diseases (e.g., Parkinson's disease), (ii) therapeutic drugs for neurodegenerative diseases (e.g., Parkinson's and Alzheimer's disease), (iii) therapeutic drugs for dopamine dysfunction (e.g., Attention Deficit Disorder), (iv) treatment of psychiatric dysfunction (e.g., depression) and (v) treatment of clinical dysfunction (e.g., migraine).

SUMMARY OF THE INVENTION

The compounds of this invention are new tropane analogs that bind to monoamine transporters. Thus, the present invention provides tropane analogs having one of the following formula:

I.

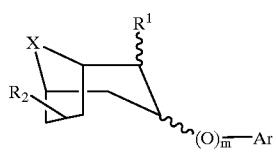

II.

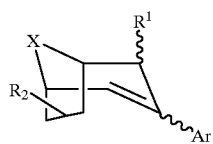

III.

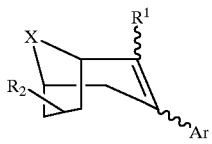

wherein:
R$_1$=COOCH$_3$, COR$_3$, lower alkyl, lower alkenyl, lower alkynyl, CONHR$_4$, or COR$_6$;
R$_2$=is a 6α, 6β, 7α or 7β substituent, which can be selected from OH, OR$_3$, F, Cl, Br, and NHR$_3$;
X=NR$_3$, CH$_2$, CHY, CYY$_1$, CO, O, S; SO, SO$_2$, NSO$_2$R$_3$, or C=CX$_1$Y with the N, C, O or S atom being a member of the ring;
X$_1$=NR$_3$, CH$_2$, CHY, CYY$_1$CO, O, S; SO, SO$_2$, or NSO$_2$R$_3$;
R$_3$=H, (CH$_2$)$_n$C$_6$H$_4$Y, C$_6$H$_4$Y, CHCH$_2$, lower alkyl, lower alkenyl or lower alkynyl;
Y and Y$_1$=H, Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, or C(CH$_3$)$_3$;
R$_4$=CH$_3$, CH$_2$CH$_3$, or CH$_3$SO$_2$;
R$_6$=morpholinyl or piperidinyl;
Ar=phenyl-R$_5$, naphthyl-R$_5$, anthracenyl-R$_5$, phenanthrenyl-R$_5$, or diphenylmethoxy-R$_5$;
R$_5$=Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);
R$_6$=morpholinyl or piperidinyl;
m=0 or 1;
n=0, 1, 2, 3, 4 or 5; and
when X is an oxygen atom or contains a carbon atom as the ring member, R$_2$ can be H;
except that when X=N, R$_1$ is not COR$_6$.

The substituents at the 2 and 3 position of the ring can be α- or β-. Although R$_1$ is illustrated in the 2-position, it should be recognized that substitution at the 3-position is also included and the position is dependent on the numbering of the tropane ring. The compounds of the present invention can be racemic, pure R-enantiomers, or pure S-enantiomers. Thus, the structural formulas illustrated herein are intended to represent each enantiomer and diastereomer of the illustrated compound.

The compounds of the present invention can be radiolabelled, for example, to assay cocaine receptors. Certain preferred compounds of the present invention have a high selectivity for the DAT versus the SERT.

The present invention also provides pharmaceutical therapeutic compositions comprising the compounds formulated in a pharmaceutically acceptable carrier.

Further, the invention provides a method for inhibiting 5-hydroxytryptamine reuptake of a monoamine transporter by contacting the monoamine transporter with a 5-hydroxytryptamine reuptake inhibiting (5-HT inhibiting) amount of a compound of the present invention. Inhibition of 5-hydroxy-tryptamine reuptake of a monoamine transporter in a mammal is provided in accord with the present invention by administering to the mammal a 5-HT inhibiting amount of a compound of the present invention in a pharmaceutically acceptable carrier. Preferred monoamine transporters for the practice of the present invention include the dopamine transporter, the serotonin transporter and the norepinephrine transporter.

In a preferred embodiment, the invention also provides a method for inhibiting dopamine reuptake of a dopamine transporter by contacting the dopamine transporter with a dopamine reuptake inhibiting amount of a compound of the present invention. Inhibition of dopamine reuptake of a dopamine transporter in a mammal is provided in accord with the present invention by administering to the mammal a dopamine inhibiting amount of a compound of the present invention in a pharmaceutically acceptable carrier.

The term "lower alky", when used herein designates aliphatic saturated branched or straight chain hydrocarbon monovalent substituents containing from 1 to about 8 carbon atoms such as methyl, ethyl, isopropyl, n-propyl, n-butyl, (CH$_2$)$_n$CH$_3$, C(CH$_3$)$_3$; etc., more preferably 1 to 4 carbons. The term "lower alkoxy" designates lower alkoxy substituents containing from 1 to about 8 carbon atoms such as methoxy, ethoxy, isopropoxy, etc., more preferably 1 to 4 carbon atoms.

The term "lower alkeny", when used herein designates aliphatic unsaturated branched or straight chain vinyl hydrocarbon substituents containing from 2 to about 8 carbon atoms such as allyl, etc., more preferably 2 to 4 carbons. The term "lower alkyny" designates lower alkynyl substituents containing from 2 to about 8 carbon atoms, more preferably 2 to 4 carbon atoms such as, for example, propyne, butyne, etc.

The terms substituted lower alkyl, substituted lower alkoxy, substituted lower alkenyl and substituted lower alkynyl, when used herein, include corresponding alkyl, alkoxy, alkenyl or alkynyl groups substituted with halide, hydroxy, carboxylic acid, or carboxamide groups, etc. such as, for example, —CH$_2$OH, —CH$_2$CH$_2$COOH, —CH$_2$CONH$_2$, —OCH$_2$CH$_2$OH, —OCH$_2$COOH, —OCH$_2$CH$_2$CONH$_2$, etc. As used herein, the terms lower alkyl, lower alkoxy, lower alkenyl and lower alkynyl are meant to include where practical substituted such groups as described above.

When X contains a carbon atom as the ring member, reference to X is sometimes made herein as a carbon group. Thus, when X is a carbon group, as that phrase is used herein, it means that a carbon atom is a ring member at the X position (i.e., the 8-position).

DETAILED DESCRIPTION OF THE INVENTION

In accord with the present invention, novel tropane compounds are provided that bind to monoamine transporters, preferably the DAT. Certain preferred compounds also have a high selectivity for the DAT versus the SERT. In one preferred embodiment of the present invention, tropane analogs are provided having substituents in the 6- or 7-position of the tropane structure. Preferred compounds of this embodiment of the invention include those having the formula:
IV.

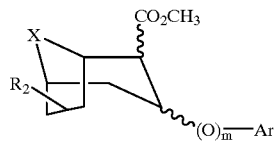

where X, Ar, R$_2$ and m have the same meaning as defined above. Particularly preferred compounds have X includes a nitrogen, carbon or oxygen atom as a ring member, R$_2$ is hydrogen, hydroxy or methoxy, and Ar is phenyl, substituted phenyl such as mono- or di-halogen substituted phenyl, or a diarylmethoxy including halogen substituted such groups.

Figure 1:
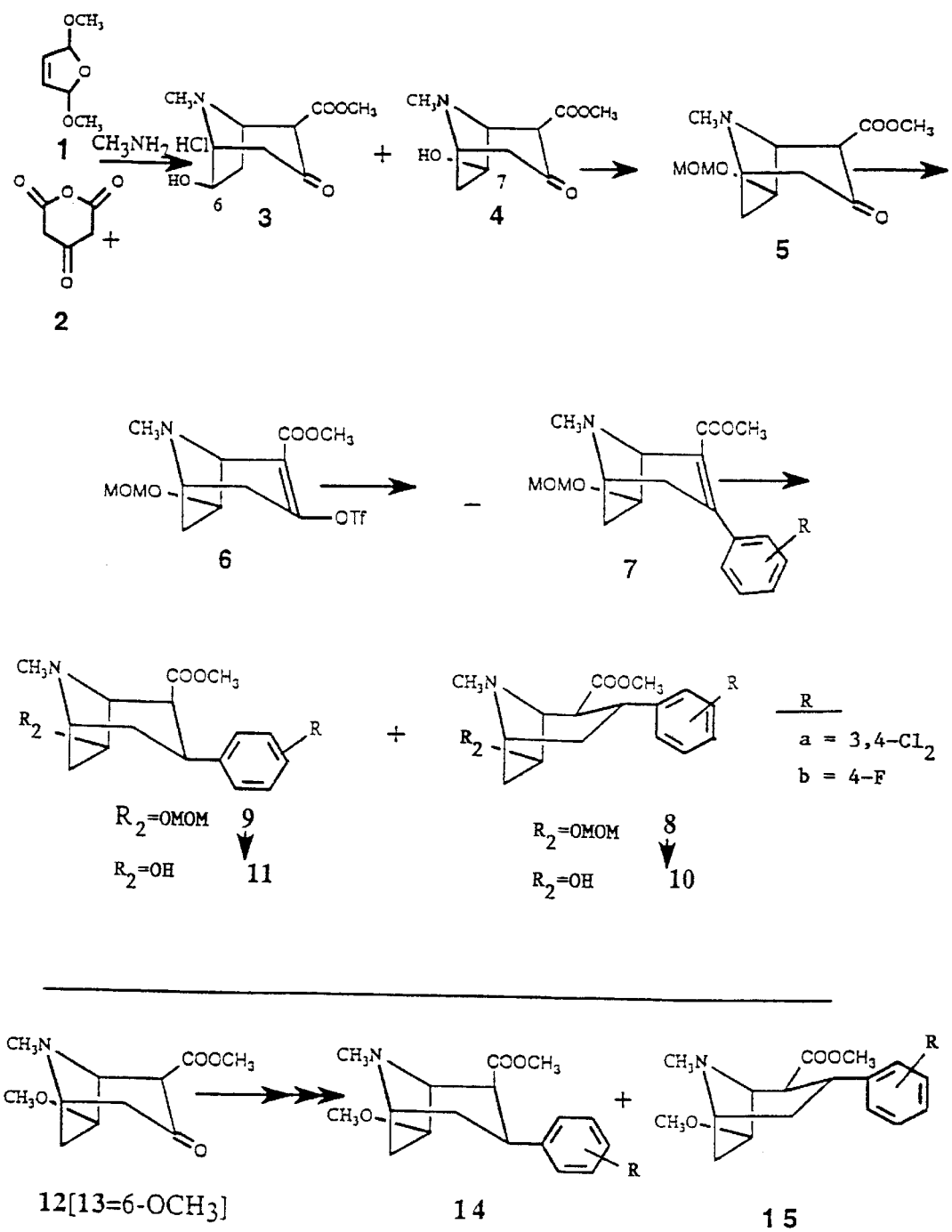
FIG. 1 illustrates a chemical reaction scheme for producing 6- or 7-substituted tropane analogs (Scheme 1).

For example, 6- and 7-hydroxy-8-azatropanes of the present invention can be prepared as shown in Scheme 1 (FIG. 1). Synthesis of these 6- and 7-oxygenated tropanes in accord with Scheme 1 is based upon a Mannich reaction. (Robinson, R. (1917), *J. Chem. Soc.* 111: 762.) Dimethoxydihydrofuran 1, is stirred for 12 h (hours) in 3N HCl and then neutralized by addition of aqueous NaOH. Methylamine hydrochloride in water, and acetone-dicarboxylic acid anhydride 2 in MeOH are added. A mixture of 6- and 7-hydroxy, 3β-keto esters 3 and 4 is obtained. The exo (β) stereochemistry of the hydroxyl group at C$_6$ (3), or C$_7$ (4), is confirmed by NMR studies.

Chromatographic separation also provides 6- and 7-methoxy compounds 12 and 13. The 6- and 7-hydroxy β-keto esters 3 and 4 are each methoxymethylated with dimethoxymethane and pTSA to provide 5. Although both 6- and 7-substituted compounds are taken through the following sequence of reactions, Scheme 1 illustrates the reaction scheme for the 7-substituted compound. Subsequent conversion (Carroll, F. I., P. Kotian, A. Dehghani, J. L. Gray, et al. (1995), *J. Med. Chem.* 38: 379–388; Keverline, K. I., P. Abraham, A. H. Lewin and F. I. Carroll (1995), *Tetrahedron Lett.* 36: 3099–3102) to the enol triflate 6 is achieved with sodium bistrimethylsilyl amide and phenyl triflimide. The alkenes 7 are then obtained (85%) by Suzuki coupling of the triflates with 3,4-dichlorophenyl boronic acid. Reduction of 7 with SmI$_2$ at −78° C., in the presence of MeOH, and subsequent chromatography affords the saturated tropanes, 8 (61%) and 9 (20%). Compound 8 exists in a twist-boat conformation while compound 9 assumes a twist-chair conformation. Finally, the methoxymethyl (MOM) group of each of 8 and 9 is removed in high yield (85%) with trimethylsilyl bromide in CH$_2$Cl$_2$ at 0° C. to give the corresponding hydroxy tropanes 10 and 11. (Chen, Z., S. Izenwasser, J. L. Katz, N. Zhu, C. L. Klein and M. L. Trudell (1996), *J. Med. Chem.* 39: 4744–4749; #214.) The alkene 7 can be treated in the same manner to remve the MOM group at that stage and provide a 6- or 7-substituted unsaturated tropane analog.

Esters can be obtained by acylation with suitable acid chlorides or anhydrides. The 7- (and 6-) methoxy, 3β-keto esters 12 (and 13) are transformed into their enol triflates and analogous transformations then provide the methoxy tropanes 14 and 15.

Biological data for representative 2-carbomethoxy-3-(3, 4-diphenyltropanes of the present invention are shown in Table 1.

TABLE 1

Inhibition of $^3$H-WIN35,428 binding to the DAT and $^3$H-citalopram binding to the SERT: cynomolgus monkey caudate-putamen

| | | | IC$_{50}$ (nM) | | Selectivity |
|---|---|---|---|---|---|
| Compound | | R | DAT | SERT | DAT V.SERT |
| 10 | 3α (boat) | OH | 1 | 1,450 | 1,450 |
| 11 | 3β (chair) | OH | 1 | 20 | 20 |
| 15 | 3α (boat) | OCH$_3$ | 92 | 5,215 | 57 |
| 14 | 3β (chair) | OCH$_3$ | 86 | 884 | 10 |

The 7-OH compounds can exhibit extremely potent and selective binding for the DAT. Thus, compound 10 manifests an IC$_{50}$<2 nM and high selectivity (DAT v. SERT>500) and the 3β compound 11 is equally potent at the DAT (IC$_{50}$=1 nM) but less selective (DAT v. SERT=20). Whereas the parent compound 2-carbomethoxy-3,4-dichlorophenyltropane is potent, (IC$_{50}$=1.09 nM) but lacks selectivity (DAT v. SERT=2), the 7β-hydroxy compounds surprisingly retain potency and are also considerably more selective (DAT v. SERT=20 for 3β (chair), =1450 for 3α (boat)). Introduction of the 7β-hydroxyl group has significantly and unexpectedly improved the selectivity of these compounds for the DAT.

These compounds are racemic. The pure enantiomers, compound 10 and compound 11, are synthesized enantiopure. Resolution is achieved by formation of the diastereomeric tartrate salts of compound 5 or by formation and separation of diastereomeric enol camphanates. Thus, the tartrate salt of protected (MOM or AcO) compound 5 is recrystallized by standard methods, well known to those skilled in the art, to provide each of the diastereomeric salts. Treatment with base provides enantiopure (1R)-compound 5 and (1S)-compound 5. Alternatively, formation of the diastereomeric enol camphanates esters of compound 5, recrystalization, and hydrolysis with LiOH also provides enantiopure (1R)-compound 5 and (1S)-compound 5. These enantiopure ketones are carried through the sequence to provide the enantiopure target compounds. Thus, 3β (chair) and 3α (boat) hydroxytropanes or various analogous alkoxytropanes can be prepared.

The potency of the 7-hydroxy and 7-methoxy anaologs of 2-carbomethoxy-3-(3,4-diphenyl tropane, 3β (chair) and 3α (boat), shown in Table 1, were determined by the Dopamine Transporter Assay and Serotonin Transporter Assay described hereinafter.

Figure 2:
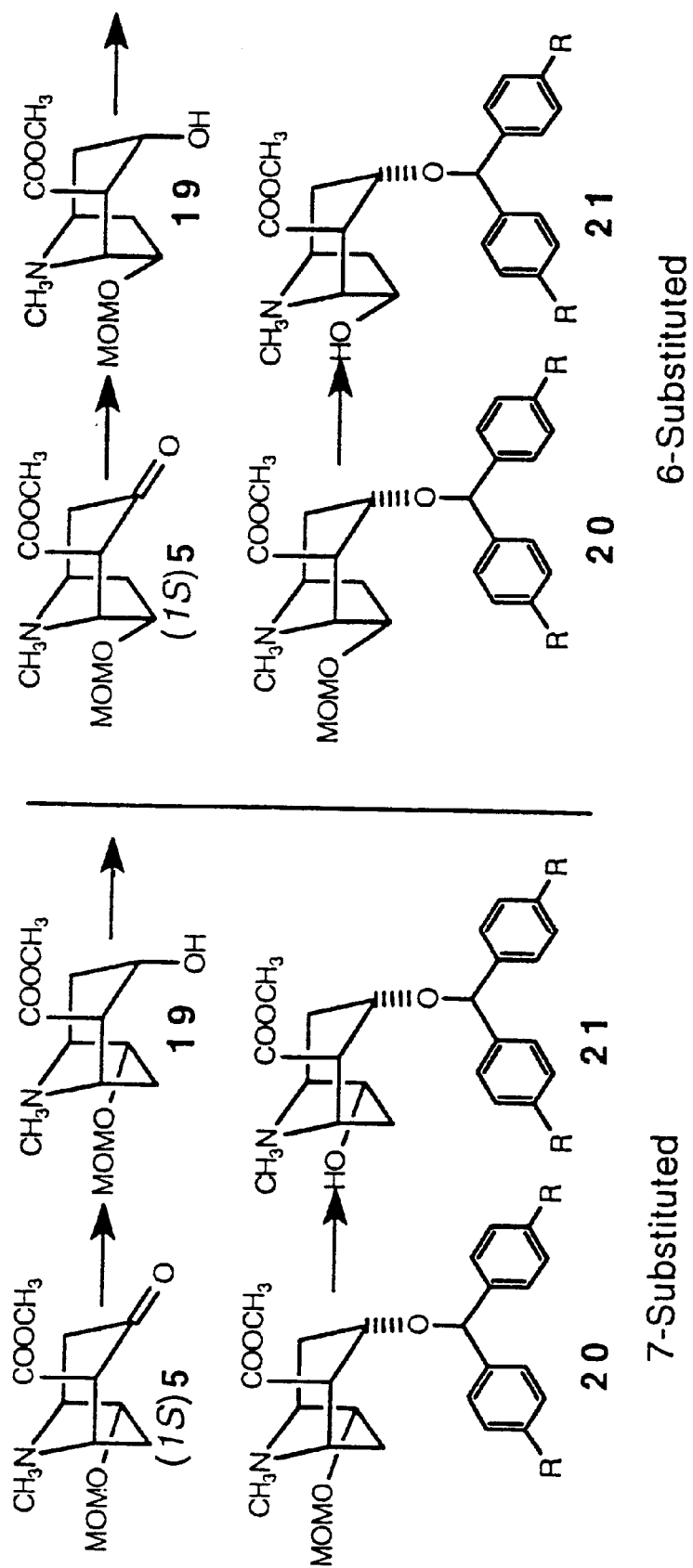
FIG. 2 illustrates a reaction scheme for the preparation of 3-diarylmethoxytropanes (Scheme 2) using a 7-substituted, 3β-keto tropane to make the corresponding 7β-OH compound.

The preparation of 3-diarylmethoxytropanes is illustrated in Scheme 2 using a 7-substituted, 3β-keto tropane to make the corresponding 7β-OH compound (see FIG. 2). The 7α-OH (as well as 6α-OH and 6β-OH) compounds are carried through an identical sequence. Other 3-aryloxytropanes can be made by analogous reaction schemes. Synthesis of the 7β-OH compound 21 is based upon prior synthetic routes. Thus, the MOM protected (1S)-keto ester 5 is reduced with LiBH(Bu$^i$)$_3$ in tetrahydrofuran (THF) to provide the 2β-COOCH$_3$-3α-OH compound 19. Alternatively, reduction can be conducted with NaBH$_4$, to provide a mixture of the 2α, 2β, and 3α, 3β substituted compounds. The 2α-COOCH$_3$-3α-OH compound can be inverted upon treatment with NaHCO$_3$ to provide the preferred 2β-COOCH$_3$-3α-OH 19. Reaction of compound 19 with diarylmethyl chloride (van der Zee 1980) gives the MOM protected compound 20 which is deprotected with trimethylsilyl bromide (TMSBr) in CH$_2$Cl$_2$ to yield the desired target compounds 21. The aryl ring can be substituted with one or more halide atoms, preferably chloride or iodide, hydroxy groups, nitro groups, amino groups including mono- and di-alkyl substituted groups having from 1–8 carbon atoms, cyano groups, lower alkyl groups having from 1–8 carbon atoms, lower alkoxy groups having from 1–8 carbon atoms, lower alkenyl groups having from 2–8 carbon atoms, lower alkynyl groups having from 2–8 carbon atoms, and combinations of such substituents. Preferred aryl groups have substituents including Br, Cl, I, F, OH, OCH$_3$, CF$_3$, NO$_2$, NH$_2$, CN, NHCOCH$_3$, N(CH$_3$)$_2$, (CH$_2$)$_n$CH$_3$ where n=0–6, COCH$_3$, C(CH$_3$)$_3$, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, allyl, isopropyl and isobutyl.

Potent "6,7-bridge" hydroxy compounds of the tropane analogs of the present invention, e.g., the 8-aza family, can be demethylated and realkylated with a variety of alkyl and alkyl aryl groups. Thus, for example 21 is treated with ACE-Cl to provide the nor compound or demethylation can be conducted prior to deprotection by treatment of 20 with ACE-Cl in presence of 2,6-lutidine. Reaction with suitable alkyl chlorides in the presence of K$_2$CO$_3$ or alternately with KF/celite then provides N-substituted compounds such as N—(CH$_2$)$_n$—Ar (n=1–3; Ar=phenyl or halophenyl). The MOM group is removed with TMSBr.

8-oxatropanes, in accord with the present invention, can be potent inhibitors of monoamine transporters. 6- and 7-Hydroxy-8-oxa-3-aryl tropanes are particularly preferred compounds of the present invention. Examples of such preferred compounds of the present invention have the following formula:

V.

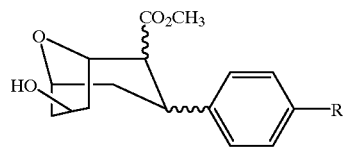

where R is preferably H, 4-F, 4-Cl, 4-Br, 4-I, 4-CH$_3$, or the aryl group is a 3,4 dihalo substituted phenyl such as, for example, 3,4-dichloro.

Figure 3:
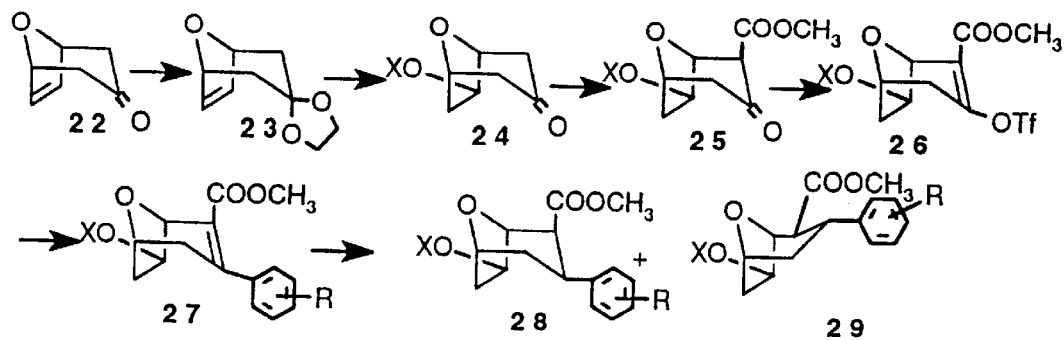
FIG. 3 illustrates a reaction scheme for the preparation of 8-oxatropanes (Scheme 3).
Figure 4:
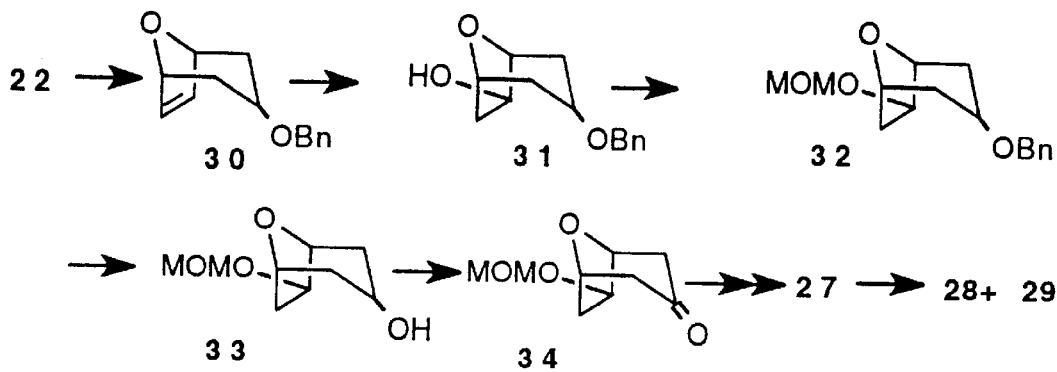
FIG. 4 illustrates an alternative reaction scheme for the preparation of 8-oxatropanes (Scheme 4).

The syntheses of 8-oxatropanes can be accomplished by either of the two routes (Schemes 3 and 4) illustrated herein. Thus, following Scheme 3 (FIG. 3), the ketone 22, prepared as described by Lampe and Hoffman (Chem. Commun. (1996): 1931–1932) is protected as the ketal 23 (ethylene glycol, p-toluene sulfonic acid (pTSA)) and then hydroborated with LiBH(Bu$^i$)$_3$ (Bu$^i$=iso-butyl) followed by oxidative work-up with alkaline H$_2$O$_2$ (Lautens, M. and S. Ma (1996), Tetrahedron Lett. 37: 1727–1730) to provide the ketone 24 (X=H). Protection with dimethoxymethane and pTSA then provides protected compound 24 (X=MOM). Introduction of the 2-COOCH$_3$ group is effected with dimethylcarbonate and sodium hydride (Meltzer, P. C., A. Y. Liang and B. K. Madras (1994), J. Med. Chem. 37: 2001–2010) to provide compound 25 (X=MOM). Introduction of this 2-COOCH$_3$ group is not specific. However, this is an advantage because racemic 2-COOCH$_3$-oxabicycles, both 6- and 7-substituted, are obtained. These positional isomers are separable by column chromatography. Resolution is accomplished through the enol camphanate route described earlier. Conversion to the enol triflate 26 is accomplished with sodium bistrimethylsilyl amide and phenyl triflimide. Suzuki coupling of the triflates with the relevant aryl boronic acid obtains the alkenes 27. Reduction of 27 with SmI$_2$ at −78° C., with MeOH as the proton source, and subsequent chromatography affords the saturated protected oxabicycles 28 and 29. Finally, the MOM group of each of 28 and 29 is removed with trimethylsilyl bromide in CH$_2$Cl$_2$ at 0° C. to give the corresponding hydroxy tropanes 28 (X=H) and 29 (X=H). Deprotecting compound 27 can make the corresponding unsaturated oxatropanes.

Alternatively, using the longer route (Scheme 4), the ketone 22 is converted to the benzyl protected alcohol 31. Both the (−)-compound 31 and the (+)-compound 31 have been prepared in >96% ee by use of (−)-(Ipc)$_2$BH or (+)-(Ipc)$_2$BH respectively. (Lampe, T. F. J. and H. M. R. Hoffmann (1996), Chem. Commun.: 1931–1932.) Protection of the hydroxy group with dimethoxymethane and pTSA provides compound 32 (X=MOM). Catalytic hydrogenolysis then provides the 3-ol compound 33. Oxidation under mild Dess-Martin conditions (Dess, D. B. and J. C. Martin (1983). J. Org. Chem. 48: 4155) gives the desired ketones 34 (X=MOM) which are carried through the sequence described above to provide compounds 28 and 29.

In another preferred embodiment of the present invention, preferred 8-oxatropanes and 8-carbatropanes include those having alkenyl and alkynyl groups on the 3-aryl ring, particularly of the 2-COOCH$_3$ tropanes, to enhance potency at the SERT. Particularly preferred examples of such compounds have the following formula:
VI.

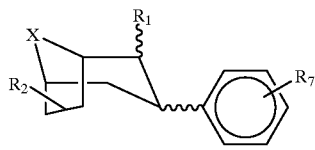

where X is an oxygen or a carbon group such as, for example, $CH_2$, CHY, $CYY_1$, CO, or $C=CX_1Y$ where $X_1$, Y and $Y_1$ are defined above, and $R_7$ is a lower alkenyl or lower alkynyl group having from about 2 to about 8 carbon atoms. Particularly preferred lower alkenyl and lower alkynyl groups are ethenyl, propenyl, butenyl, propynyl, butynyl and methylpropynyl.

Figure 5:
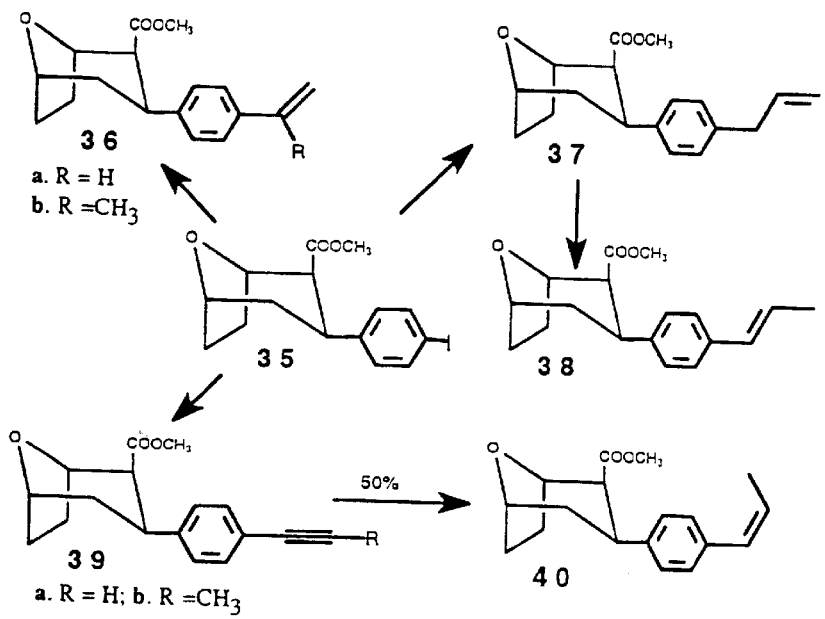
FIG. 5 illustrates a reaction scheme for the preparation of 3-aryl(substituted)-8-oxatropanes (Scheme 5).

Introduction of such functionality in the 8-oxa compounds can be accomplished following the reported synthetic route for the 8-aza compounds. (Blough, B. E., P. Abraham, A. H. Lewin, M. J. Kuhar, J. W. Boja and F. I. Carroll (1996), *J. Med. Chem.* 39: 4027–4035.) Iodo compounds are prepared as precursors for the 4-alkenyl and 4-alkynyl compounds shown in Scheme 5 (see FIG. 5). Reduction of the octenes 47 (Scheme 6) (R=I) with $SmI_2$ in THF/MeOH at −78° C. provides a mixture of the 3β and 3α compounds 35. In general, when trifluoroacetic acid is used, the major products are the 2β, 3α-boat conformers. The minor products are the 2β, 3β-chair conformers. With water as proton source, a 1:1 mixture is generally obtained. Chemical shift, coupling constants, and nuclear Overhauser effect ("nOe") analyses confirm that the 2β-carbomethoxy compounds are exclusively obtained upon $SmI_2$ reduction of the octenes. Only 3β compounds are presented in the scheme. However, compounds in 3α and 3β conformation are similarly prepared. Racemates and enantiopure compounds can also be prepared by similar techniques well known to those skilled in the art. Compound 35 is reacted with CuI and bis(triphenylphosphine)palladium (II) chloride and trimethyl silylacetylene. The product is desilylated with t-butyl ammonium fluoride to provide the 4-alkynyl compounds 39a. The same reaction, using propyne, provides compound 39b, although no deprotection is required here. Reduction of compound 39b over Lindlar's catalyst at 60 psi provides the Z-ene 40. The E-ene 38 is obtained via the allyl compound 37. Thus, compound 35 is reacted with allyltributyltin and tetrakis(triphenyl-phosphine)palladium to provide compound 37, which is quantitatively isomerized to compound 38.

Compounds 36a and b are prepared upon reaction of compound 35, in the presence of $ZnCl_2$ and bis(triphenylphosphine)palladium (II) chloride, with vinylmagnesium bromide, or 2-bromo-propene and n-butyl lithium, respectively.

The 3α compounds are obtained by identical chemistry. Also, the enantiopure end-products required are carried through identical chemistry for 3α and 3β diastereomers starting with enantiopure compound 35 obtained from enantiopure ketones (1R)-45 and (1S)-45. Conformational and configurational assignments demonstrate that the carbomethoxy is in the 2β-configuration. Further, the 3α vs. 3β conformers are readily identified.

A comparison of the binding potency of the 8-oxabicycles with the 8-azabicycles shows that, although the most potent in both classes are almost equipotent ($IC_{50}$=1–3 nM), the less potent compounds (R=H, F) are typically weaker in the 8-oxa than 8-aza series.

The enol triflate is reacted with the appropriate polyaromatic boronic acids (Thompson, W. J. and J. Gaudino (1984), *J. Org. Chem.* 49: 5237–5243) to provide the 2,3-enes. $SmI_2$ reduction gives 3α and 3β conformers:
VII.

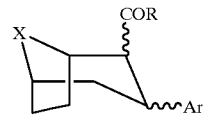

where X is an oxygen atom or a carbon group, Ar is preferably 4-substituted phenyl, naphthyl, anthracenyl or phenanthrenyl and R is preferably lower alkyl, lower alkoxy or amino, as defined above. The compounds are prepared as racemates and pairs of enantiomers.

Enantiomers and diastereomers can be separated by silica gel chromatography using 2% ammonia in ethyl acetate as the eluent, or other solvent systems as necessary. Compounds from the above series are hydrolyzed (LiOH) and treated with oxalyl chloride followed by amines such as morpholine or piperidine to provide amides.

2,3- (and 3,4-) Unsaturated 8-aza- and 8-oxa-tropanes are additional preferred embodiments of the present invention. Examples of preferred such compounds have the following formula:
VIII.

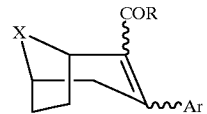

where X is preferably oxygen, N-alkyl or a carbon moiety, R is preferably morpholinyl, piperidinyl or methoxy, Ar is preferably phenyl or naphthyl either of which can be substituted with halogen, alkenyl having 2–8 carbon atoms or alkynyl having 2–8 carbon atoms such as, for example, 4-Cl, 4-F, 4-Br, 4-I, 3,4-$Cl_2$, ethenyl, propenyl, butenyl, propynyl, butynyl, etc.

Figure 6:
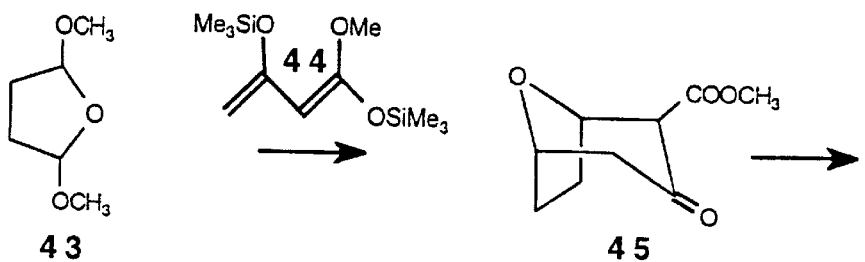
FIG. 6 illustrates a reaction scheme for the preparation of 2-carbomethoxy-3-aryl-8-oxabicyclo(3.2.1)octenes (Scheme 6).
Figure 6:
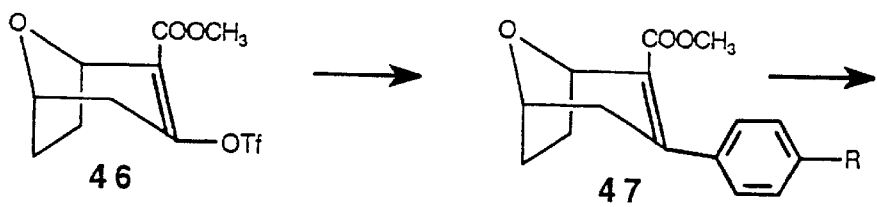
Figure 7:
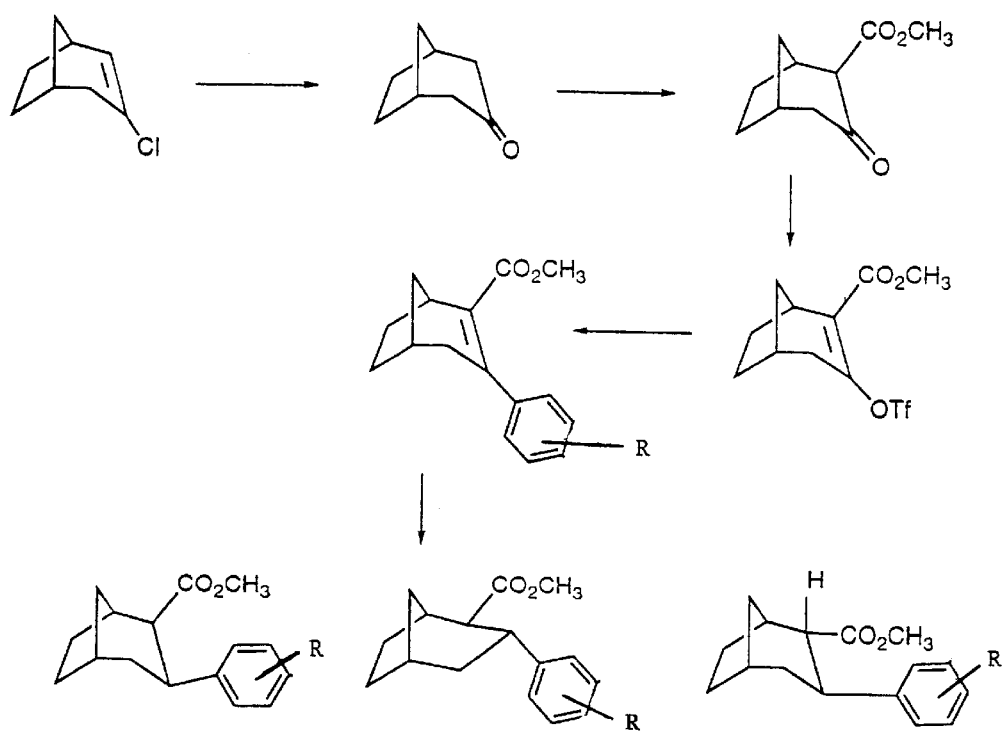
FIG. 7 illustrates a reaction scheme for the preparation of 8-carbatropanes (Scheme 7).

The synthesis of the 2,3-unsaturated 8-aza- and 8-oxa-tropanes is exemplified in Scheme 6 (see FIG. 6). The 3-(substituted aryl)-8-oxabicyclo(3.2.1)octanes can be obtained from the keto ester 45. Thus, 2,5-dimethoxytetrahydrofuran 43 is reacted with 1,3-bis(trimethylsiloxy)-1-methoxybuta-1,3-diene 44 in $CH_2Cl_2$ in the presence of $TiCl_4$ to give the ketone 45. The ketone 45 is then converted to compound 46 by reaction with N-phenyltrifluoromethanesulfonimide and sodium bis(trimethylsilyl)amide in THF. The enol triflate 46 is coupled with arylboronic acids in the presence of tris(dibenzylideneacetone)dipalladium(0) to provide the aryl octenes 47.

Compounds 47e and f are synthesized from enantiopure compound (1R)-45 and compound (1S)-45. Alternatively, a diastereomeric mixture of enol camphanates is prepared upon reaction of compounds (1R/S)-45 with (S)-(−)-camphanyl chloride in THF. recrystalization from $CH_2Cl_2$/hexane then gives the pure diastereomer (1R)-enol camphanate as evidenced by NMR. The residual mixture of enol camphanate diastereomers is treated with LiOH to produce compounds (1R/1S)-45 which is then reacted with (R)-(+)-camphanyl chloride. Recrystalization of this enol camphanate then gives the pure (1S)-enol camphanate diastereomer. Quantitative hydrolysis of the enantiomerically pure individual camphanate esters with LiOH provides ketones (1S)-45 and (1R)-45 (chiral HPLC OC column: (1R)-45 and (1S)-45 >96% ee for each of the enantiomers). The purified enantiomers are then subjected to the sequence of steps described earlier to obtain the enantiomerically pure 8-oxatropene analogs, 27e and f (see Scheme 3, FIG. 3). Absolute configuration was confirmed by X-ray structural analysis. Isomerization of the 2,3-ene to provide the 3,4-enes is achieved with base.

Biological data for representative 2,3-enes of the present invention having a 3-(3,4-dichloro)phenyl substituent are shown in Table 2.

TABLE 2

Inhibition of $^3$H-WIN35,428 binding to the DAT and $^3$H-citalopram binding to the SERT in cynomolgus monkey caudate-putamen.

| Compound | | R/S | IC$_{50}$ (nM) | | Selectivity |
| | | | DAT | SERT | DAT/SERT |
| --- | --- | --- | --- | --- | --- |
| 47e | 8-O | (1R) | 4.6 | 2,120 | 461 |
| 47f | 8-O | (1S) | 58.2 | 46,730 | 802 |
| 48 | 8-NCH$_3$ | (1R) | 1.1 | 867 | 790 |

The (1R) enantiomer 47e binds potently to the DAT (IC$_{50}$=4.6 nM) and very weakly at the SERT (IC$_{50}$=2,120 nM) and is ca. 460-fold selective. Surprisingly and unexpectedly, the (1S) enantiomer 47f retains potency (DAT: IC$_{50}$=58.2 nM) and substantial selectivity DAT/SERT=800). The 8-amine analogs of these compounds can be prepared via analogous enol triflate chemistry. Thus, 2-carbomethoxytropane-2-one is similarly converted to its enol triflate and coupled with 3,4-dichlorophenyl boronic acid to provide compound 48. Compound 48 is among the most potent and selective (790-fold) compounds (DAT IC$_{50}$=1.1 n-M; SERT IC$_{50}$=867 n). These compounds offer an opportunity to differentiate binding to the SERT vs. the DAT, as well as to take advantage of the different biological profiles (biological t$_{1/2}$, toxicity, metabolism) that these compounds offer.

In accord with another preferred embodiment of the present invention, the 2,3- (and 3,4-) didehydro tropanes and 8-oxatropanes have been hydroxylated or alkoxylated at the 6- and 7-positions to provide compounds capable of intramolecular hydrogen bonding to the 8-oxa and 8-aza positions. The selectivity observed in the 2,3-ene and the 7-OH compounds provides synergism and offers extremely potent and selective compounds. The 7β-hydroxy tropanes 10 and 11 are potent and selective. The (1R) 2,3-ene enantiomer 47e binds potently and selectively to the DAT and the (1R) 8-aza-2,3-ene 48 is among the most potent and selective DAT inhibitors. Compounds exhibiting both functionalities are particularly preferred. The conversion of an enol triflate via Suzuki coupling with appropriate arylboronic acids provides the preferred compounds (see also Scheme 1, FIG. 1). Such compounds, i.e., bicyclo(3.2.1) octanes, include compounds having the following formula: IX.

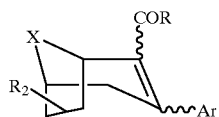

where X is preferably O, NCH$_3$ or CH$_2$, R is preferably morpholinyl, piperidinyl or methoxy, R$_2$ is preferably hydroxy or methoxy in the 6- or 7-position, Ar is preferably phenyl or naphthyl either of which can be substituted with halogen, alkenyl having 2–8 carbon atoms or alkynyl having 2–8 carbon atoms such as, for example, 4-Cl, 4-F, 4-Br, 4-I, 3,4-Cl$_2$, ethenyl, propenyl, butenyl, propynyl, butynyl, etc.

These compounds can be prepared either as free bases or as a pharmacologically active salt thereof such as hydrochloride, tartrate, sulfate, naphthalene-1,5-disulfonate or the like.

The present invention also provides pharmaceutical compositions, preferably comprising the compounds of the present invention in a pharmaceutically acceptable carrier. Pharmaceutically acceptable carriers are well known to those skilled in the art. In a preferred embodiment, the pharmaceutical composition is a liquid composition in pyrogen-free, sterilized container or vial. The container can be unit dose or multidose.

The compounds and pharmaceutical preparations of the present invention can be used to inhibit the 5-hydroxytryptamine reuptake of a monoamine transporter, particularly reuptake by the dopamine transporter, serotonin transporter or norepinephrine transporter. An effective dose of the compound is administered to a patient based on IC$_{50}$ values determined in vitro. The route of administration can be varied but is principally selected from intravenous, nasal and oral routes. The effective dose can vary depending upon the mode of administration as is well known in the art.

Dysfunction of dopamine neurons has been implicated in several neuropsychiatric diseases. Imaging of the dopamine neurons offers important clinical information relevant to diagnosis and therapeutic treatments. Dopamine neurons produce dopamine, release the neurotransmitter and remove the released dopamine with a dopamine transporter protein. Compounds that bind to the dopamine transporter are effective measures of dopamine neurons and can be transformed into imaging agents for PET and for SPECT imaging. In identifying a suitable compound for the dopamine transporter, an essential first step is to measure the affinity and selectivity of a candidate at the dopamine transporter. The affinity is measured by conducting radioreceptor assays. A radiolabeled marker for the transporter, e.g., ($^3$H)WIN 35,428, is incubated with the unlabeled candidate and a source of the transporter, usually brain striatum. The effect of various concentrations of the candidate on inhibiting (3H)WIN 35,428 binding is quantified. The concentration of the compound that inhibits 50% of ($^3$H)WIN 35,428 bound to the transporter (IC$_{50}$ value) is used as a measure of its affinity for the transporter. A suitable range of concentrations of the candidate typically is 1–10 nM.

It is also important to measure the selectivity of the candidate of the dopamine compared with the serotonin transporter. The serotonin transporter is also detectable in the striatum, the brain region with the highest density of dopamine neurons and in brain regions surrounding the striatum. It is necessary to determine whether the candidate compound is more potent at the dopamine than the serotonin transporter. If more selective (>10-fold), the probe will permit accurate measures of the dopamine transporter in this region of interest or will provide effective treatment modality for the dopamine transporter. Therefore, a measure of probe affinity of the serotonin transport is conducted by assays paralleling the dopamine transporter assays. ($^3$H) Citalopram is used to radiolabel binding sites on the serotonin transporter and competition studies are conducted with the candidate compound at various concentrations in order to generate an IC$_{50}$ value.

This invention will be illustrated further by the following examples. These examples are not intended to limit the scope of the claimed invention in any manner. The Examples provide suitable methods for preparing compounds of the present invention. However, those skilled in the art may make compounds of the present invention by any other suitable means. As is well known to those skilled in the art, other substituents can be provided for the illustrated compounds by suitable modification of the reactants.

All exemplified target compounds are fully analyzed (mp, TLC, CHN, GC and/or HPLC) and characterized ($^1$H NMR, $^{13}$C NMR, MS, IR) prior to submission for biological evaluation. The affinity of all the compounds for the DAT, SERT and NET are measured. NMR spectra are recorded on a Bruker 100, a Varian XL 400, or a Bruker 300 NMR spectrometer. Tetramethylsilane ("TMS") is used as internal standard. Melting points are uncorrected and are measured on a Gallenkamp melting point apparatus. Thin layer chromatography (TLC) is carried out on Baker Si 250F plates. Visualization is accomplished with iodine vapor, UV exposure or treatment with phosphomolybdic acid (PMA). Preparative TLC is carried out on Analtech uniplates Silica Gel GF 2000 microns. Flash chromatography is carried out on Baker Silica Gel 40 mM. Elemental Analyses are performed by Atlantic Microlab, Atlanta, Ga. and are within 0.4% of calculated values for each element. A Beckman 1801 Scintillation Counter is used for scintillation spectrometry. 0.1% Bovine Serum Albumin ("BSA") and (−)-cocaine is purchased from Sigma Chemicals. All reactions are conducted under an inert ($N_2$) atmosphere.

$^3$H-WIN 35,428 ($^3$H-CFT, 2β-carbomethoxy-3β-(4-fluorophenyl)-N-$^3$H-methyltropane, 79.4–87.0 Ci/mmol) and $^3$H-citalopram (86.8 Ci/mmol) is purchased from DuPont-New England Nuclear (Boston, Mass.). (R)-(−)-Cocaine hydrochloride for the pharmacological studies was donated by the National Institute on Drug Abuse (NIDA). Fluoxetine was donated by E. Lilly & Co. HPLC analyses are carried out on a Waters 510 system with detection at 254 nm on a Chiralcel OC column (flow rate: 1 mL/min).

EXAMPLE 1

(1R,1S) -2-Carbomethoxy-8-oxabicyclo(3.2.1)octanone

To 2,5-dimethoxytetrahydrofuran (39.6 g, 0.3 mol) in $CH_2Cl_2$ (anhydrous, 200 mL) at −78° C. under nitrogen was added $TiCl_4$ (66 mL, 0.6 mol). After stirring for 30 min, 1,3-bis(trimethylsiloxy)-1-methoxybuta-1,3-diene, 2, (Chan, T.-H. and P. Brownbridge (1980), *J. Am. Chem. Soc.* 102: 3534–3538; Danishefsky, S. and T. Kitahara (1974), *J. Am. Chem. Soc.* 96: 7807–7808) (78 g, 0.3 mol) in $CH_2Cl_2$ (anhydrous, 400 mL) was added at a rate such that the internal temperature was maintained below −55° C. The mixture was stirred for 3 h. Saturated $NaHCO_3$ was added until the mixture was neutral to pH paper. The aqueous layer was extracted with ether (3×1 L). The dried ($MgSO_4$) combined organic layers were concentrated on a rotavaporator. The residue was purified by flash chromatography (20% EtOAc/hexanes) to afford 20.5 g (37%) of 3 as a light brown oil.

EXAMPLE 2

(1R,1S)-2-Carbomethoxy-3-{((trifluoromethyl)sulfonyl) oxy}-8-oxabicyclo(3.2.1)-2-octene Sodium bistrimethylsilylamide (1.0 M solution in THF, 45 mL) was added dropwise to 2-carbomethoxy-8-oxabicyclo(3.2.1) octanone, 3, (Brownbridge, P. and T.-H. Chan (1979), *Tet. Lett.* 46: 4437–4440) (7.12 g, 38.65 mmol) in THF (100 mL) at −70° C. under nitrogen. After stirring for 30 min, N-phenyltrifluoromethanesulfonimide (15.19 g, 42.52 mmol) was added as a solid at −70° C. The reaction was allowed to warm to room temperature and was then stirred overnight. The volatiles were removed on rotavaporator. The residue was dissolved in $CH_2Cl_2$ (200 mL) and washed with $H_2O$ (100 mL) and brine (100 mL). The dried ($MgSO_4$) $CH_2Cl_2$ layer was concentrated to dryness on rotavaporator. The residue was purified by flash chromatography (10% EtOAc/hexanes) to afford 9.62 g (79%) of 4 as a pale yellow oil.

$^1$H NMR (CDCL$_3$, 100 MHz): δ 5.05 (bm, 1H) ,4.70 (t, 1H), 3.83 (s, 3H), 3.0 (dd, 1H), 2.0–2.35 (m, 5H).

EXAMPLE 3

(1R,1S)-2-Carbomethoxy-3-phenyl-8-oxabicyclo(3.2.1)-2-octene.

2-Carbomethoxy-3-{((trifluoromethyl)sulfonyl)oxy}-8-oxabicyclo(3.2.1)-2-octene (2.0 g, 6.32 mmol), phenyl boronic acid (1.02 g, 8.36 mmol), diethoxymethane (20 mL), LiCl (578 mg, 13.6 mmol), tris(dibenzylideneacetone) dipalladium(0) (247 mg, 0.25 mmol) and $Na_2CO_3$ (2 M solution, 6.1 mL) were combined and heated at reflux for 1 h. The mixture was cooled to room temperature, filtered through celite and washed with ether (100 mL). The mixture was basified with $NH_4OH$ and washed with brine. The dried ($MgSO_4$) ether layer was concentrated to dryness. The residue was purified by flash chromatography (10% EtOAc/hexanes) to afford 1.28 g (82%) of (1R,1S)-2-Carbomethoxy-3-phenyl-8-oxabicyclo(3.2.1)-2-octene as a light brown viscous oil.

$^1$H NMR (CDCl$_3$, 100 MHz): δ 7.1–7.5 (m, 5H), 5.00 (bm, 1H), 4.64 (bt, 1H), 3.52 (s, 3H), 2.95 (dd, 1H), 1.7–2.2 (m, 5H).

EXAMPLE 4

(1R,1S)-2-Carbomethoxy-3-(4-fluorophenyl)-8-oxabicyclo (3.2.1)-2-octene.

Reaction of 2-carbomethoxy-3-{((trifluoromethyl)-sulfonyl)oxy}-8-oxabicyclo(3.2.1)-2-octene (1.87 g, 5.9 mmol), 4-fluorophenyl boronic acid (1.09 g, 7.8 mmol), diethoxymethane (20 mL), LiCl (535 mg, 12.6 mmol), tris(dibenzylideneacetone)-dipalladium(0) (230 mg, 0.25 mmol) and $Na_2CO_3$ (2 M solution, 5.7 mL), as described above, gave 1.36 g (88%) of (1R,1S)-2-carbomethoxy-3-(4-fluorophenyl)-8-oxabicyclo(3.2.1)-2-octene as a light brown viscous oil.

$^1$H NMR (CDCl$_3$, 100 MHz): δ 7.0–7.2 (m, 4H), 5.00 (bm, 2H), 4.64 (bt, 1H), 3.52 (s, 3H), 2.95 (dd, 1H), 1.7–2.2 (m, 5H).

EXAMPLE 5

(1R,1S)-2-Carbomethoxy-3-(4-chlorophenyl)-8-oxabicyclo (3.2.1)-2-octene.

Reaction of 2-carbomethoxy-3-{((trifluoromethyl) sulfonyl)oxy}-8-oxabicyclo(3.2.1)-2-octene (1.0 g, 3.16 mmol), 4-chlorophenyl boronic acid (653 mg, 4.17 mmol), diethoxymethane (10 mL), LiCl (286 mg, 6.75 mmol), tris(dibenzylideneacetone)-dipalladium(0) (123 mg, 0.13 mmol) and $Na_2CO_3$ (2M solution, 3.0 mL), as described above, gave 0.81 g (92%) of (1R,1S)-2-carbomethoxy-3-(4-chlorophenyl)-8-oxabicyclo(3.2.1)-2-octene as a light brown viscous oil.

$^1$H NMR (CDCl$_3$, 100 MHz): δ 7.0–7.4 (m, 4H), 5.00 (bm, 1H), 4.64 (bt, 1H), 3.52 (s, 3H), 2.95 (dd, 1H), 1.7–2.2 (m, 5H).

EXAMPLE 6

(1R,1S)-2-Carbomethoxy-3-(3,4-dichlorophenyl)-8-oxabicyclo(3.2.1)-2-octene.

Reaction of 2-carbomethoxy-3-{((trifluoromethyl)-sulfonyl)oxy}-8-oxabicyclo(3.2.1)-2-octene (1.0 g, 3.16 mmol), 3,4-dichlorophenyl boronic acid (796 mg, 4.17 mmol), diethoxymethane (10 mL), LiCl (286 mg, 6.75 mmol), tris(dibenzylideneacetone)-dipalladium(0) (123 mg, 0.13 mmol) and $Na_2CO_3$ (2 M solution, 3.0 mL), as described above, gave 0.96 g (97%) of (1R,1S)-2-Carbomethoxy-3-(3,4-dichlorophenyl)-8-oxabicyclo(3.2.1)-2-octene as a light brown viscous oil.

$^1$H NMR ($CDCl_3$, 100 MHz): δ 6.9–7.5 (m, 3H), 5.00 (bm, 1H), 4.64 (bt, 1H), 3.52 (s, 3H), 2.95 (dd, 1H), 1.7–2.2 (m, 5H).

EXAMPLE 7

(1R,1S)-2β-Carbomethoxy-3β-phenyl-8-oxabicyclo(3.2.1)octane
and
(1R,1S)-2β-Carbomethoxy-3α-phenyl-8-oxabicyclo(3.2.1)octane.

To 2-carbomethoxy-3-phenyl-8-oxabicyclo(3.2.1)-2-octene (1.17 g, 4.8 mmol) in THF (10 mL) at −70° C. under $N_2$ was added $SmI_2$ (0.1 M in THF, 215 mL, 21.5 mmol). After the mixture was stirred for 30 min, MeOH (anhydrous, 25 mL) was added. The mixture was stirred at −70° C. for a further 2 h. The mixture was quenched with TFA (5 mL) and $H_2O$ (100 mL). After warming to 0° C., $NH_4OH$ was added to attain a pH 11 and the mixture was then stirred for 30 min. The mixture was filtered through celite and washed with ether (400 mL) and then saturated with $Na_2S_2O_3$. The ether layer was washed with brine. The dried ($MgSO_4$) ether layer was concentrated to dryness. The isomers were separated by gravity column chromatography (10% EtOAc/hexanes) to afford 789 mg (67%) of (1R,1S)-2β-carbomethoxy-3α-phenyl-8-oxabicyclo(3.2.1)octane as a white solid, mp. 96.5–98° C.; and 270 mg (23%) of (1R,1S)-2β-carbomethoxy-3β-phenyl-8-oxabicyclo(3.2.1)octane as a white solid, mp. 102.5–104° C.

$^1$H NMR ($CDCl_3$, 100 MHz) ((1R,1S)-2β-Carbomethoxy-3β-phenyl-8-oxabicyclo(3.2.1)octane): δ 7.25 (bs, 5H), 4.65 (m, 2H), 3.48 (s, 3H), 3.25 (dt, 1H), 2.6–3.0 (m, 2H), 1.5–2.3 (m, 5H). Elemental analysis calc. for $C_{15}H_{18}O_3$: C, 73.14 H, 7.37; Found C, 73.07, H, 7.40.

$^1$H NMR ($CDCl_3$, 100 MHz) ((1R,1S)-2β-Carbomethoxy-3α-phenyl-8-oxabicyclo(3.2.1)octane): δ 7.25 (bs, 5H), 4.51 (bm, 2H), 3.58 (s, 3H), 3.25 (dt, 1H), 2.51 (dd, 1H), 2.38 (m, 1H), 1.6–2.2 (m, 4H), 1.41 (ddd, 1H). Elemental analyses calc. for $C_{15}H_{18}O_3$: C, 73.14, H, 7.37; Found C, 73.02, H, 7.41.

EXAMPLE 8

(1R,1S)-2β-Carbomethoxy-3β-(4-fluorophenyl)-8-oxabicyclo(3.2.1)octane
and
(1R,1S)-2β-Carbomethoxy-3α-(4-fluorophenyl)-8-oxabicyclo(3.2.1)octane.

Reaction of 2-carbomethoxy-3-(4-fluorophenyl)-8-oxabicyclo(3.2.1)-2-octene (1.33 g, 5.07 mmol) in THF (10 mL) and $SmI_2$ (0.1 M in THF, 230 mL, 23.0 mmol), as described above, gave 834 mg (62%) of (1R,1S)-2β-Carbomethoxy-3α-(4-fluorophenyl)-8-oxabicyclo(3.2.1)octane as a white solid, mp. 58–60° C.; and 300 mg (22%) of (1R,1S)-2β-Carbomethoxy-3β-(4-fluorophenyl)-8-oxabicyclo(3.2.1)octane as a white solid, mp. 118–120.5° C.

$^1$H NMR ($CDCl_3$, 400 MHz) ((1R,1S)-2β-Carbomethoxy-3β-(4-fluorophenyl)-8-oxabicyclo(3.2.1)octane): δ 6.9–7.2 (m, 4H), 4.65 (bm, 2H), 3.48 (s, 3H), 3.17 (dt, 1H), 2.78 (d, 1H), 2.73 (dt, 1H), 2.13 (m, 1H), 2.05 (m, 1H), 1.90 (m, 1H), 1.78 (m, 1H), 1.59 (m, 1H). Elemental analysis calc. for $C_{15}H_{17}O_3F$: C, 68.16, H, 6.48; Found C, 67.88, H, 6.44.

$^1$H NMR ($CDCl_3$, 400 MHz) ((1R,1S)-2β-Carbomethoxy-3α-(4-fluorophenyl)-8-oxabicyclo(3.2.1)octane): δ 6.9–7.2 (m, 4H), 4.48 (bm, 2H), 3.58 (s, 3H), 3.20 (dt, 1H), 2.44 (dd, 1H), 2.38 (m, 1H), 2.12 (m, 1H), 2.00 (m, 1H), 1.75 (m, 1H), 1.63 (m, 1H), 1.32 (ddd, 1H). Elemental analysis calc. for $C_{15}H_{17}O_3F$: C, 68.16, H, 6.48; Found C, 68.10, H, 6.52.

EXAMPLE 9

(1R,1S)-2β-Carbomethoxy-3β-(4-chlorophenyl)-8-oxabicyclo(3.2.1)octane
and
(1R,1S)-2β-Carbomethoxy-3α-(4-chlorophenyl)-8-oxabicyclo(3.2.1)octane Reaction of 2-carbomethoxy-3-(4-chlorophenyl)-8-oxabicyclo(3.2.1)-2-octene (808 mg, 2.9 mmol) in THF (8 mL) and $SmI_2$ (0.1 M in THF, 130 mL, 13.0 mmol), as described above, gave 418 mg (51%) of (1R,1S)-2β-Carbomethoxy-3α-(4-chlorophenyl)-8-oxabicyclo(3.2.1)octane as a white solid, mp. 89–90° C.; and 152 mg (19%) of (1R,1S)-2β-carbomethoxy-3β-(4-chlorophenyl)-8-oxabicyclo(3.2.1)octane as a white solid, mp. 116–117° C.

$^1$H NMR ($CDCl_3$, 100 MHz) ((1R,1S)-2β-Carbomethoxy-3β-(4-chlorophenyl)-8-oxabicyclo(3.2.1)octane): δ 7.1–7.4 (m, 4H), 4.65 (m, 2H), 3.48 (s, 3H), 3.20 (dt, 1H), 2.6–2.9 (m, 2H), 1.5–2.3 (m, 5H). Elemental analysis calc. for $C_{15}H_{17}O_3Cl$: C, 64.17, H, 6.10, Cl, 12.63; Found C, 64.01 H, 6.09, Cl, 12.51.

$^1$H NMR ($CDCl_3$, 100 MHz) ((1R,1S)-2β-Carbomethoxy-3α-(4-chlorophenyl)-8-oxabicyclo(3.2.1)octane): δ 7.1–7.3 (m, 4H), 4.51 (bm, 2H), 3.58 (s, 3H), 3.25 (dt, 1H), 2.51 (dd, 1H), 2.38 (m, 1H), 1.6–2.2 (m, 4H), 1.35 (ddd, 1H). Elemental analysis calc. for $C_{15}H_{17}O_3Cl$: C, 64.17, H, 6.10, Cl, 12.63; Found C, 64.29 H, 6.12, Cl, 12.54.

EXAMPLE 10

(1R,1S)-2β-Carbomethoxy-3β-(3,4-dichlorophenyl)-8-oxabicyclo(3.2.1)octane
and
(1R,1S)-2β-Carbomethoxy-3α-(3,4-dichlorophenyl)-8-oxabicyclo(3.2.1)octane Reaction of 2-carbomethoxy-3-(3,4-dichlorophenyl)-8-oxabicyclo(3.2.1)-2-octene (829 mg, 2.65 mmol) in THF (5 mL) and $SmI_2$ (0.1 M in THF, 119 mL, 11.9 mmol), as described above, gave 455 mg (55%) of (1R,1S)-2β-carbomethoxy-3α-(3,4-dichlorophenyl)-8-oxabicyclo(3.2.1)octane as a white solid, mp. 88.5–90° C.; and 115 mg (14%) of (1R,1S)-2β-carbomethoxy-3β-(3,4-dichlorophenyl)-8-oxabicyclo(3.2.1)octane as a white solid, mp. 132–133.5° C.

$^1$H NMR ($CDCl_3$, 100 MHz) ((1R,1S)-2β-Carbomethoxy-3β-(3,4-dichlorophenyl)-8-oxabicyclo(3.2.1)octane): δ 7.0–7.5 (m, 3H), 4.65 (bm, 2H), 3.55 (s, 3H), 3.20 (dt, 1H), 2.6–2.9 (m, 2H), 1.5–2.3 (m, 5H).

$^1$H NMR ($CDCl_3$, 100 MHz) ((1R,1S)-2β-Carbomethoxy-3β-(3,4-dichlorophenyl)-8-oxabicyclo(3.2.1)octane): δ 7.0–7.5 (m, 3H), 4.51 (bm, 2H), 3.60 (s, 3H), 3.20 (dt, 1H), 2.51 (dd, 1H), 1.6–2.6 (m, 5H), 1.30 (ddd, 1H).

EXAMPLE 11

2-Carbomethoxy-3-(4-bromophenyl)-8-oxabicyclo(3.2.1)-2-octene.

Reaction of 2-carbomethoxy-3-{((trifluoromethyl)sulfonyl)oxy}-8-oxabicyclo(3.2.1)-2-octene (1.0 g, 3.16 mmol), 4-bromophenyl boronic acid (1.0 g, 4.98 mmol), diethoxymethane (10 mL), LiCl (286 mg, 6.75 mmol), tris(dibenzylideneacetone)-dipalladium(0) (123 mg, 0.134 mmol) and Na$_2$CO$_3$ (2 M solution, 3.0 mL), as described above, gave 416 mg (41%) of 2-carbomethoxy-3-(4-bromophenyl)-8-oxabicyclo(3.2.1)-2-octene as a clear viscous oil.

$^1$H NMR (CDCl$_3$, 100 MHz): δ 6.9–7.6 (q, 4H), 5.00 (bm, 1H), 4.64 (t, 1H), 3.52 (s, 3H), 2.95 (dd, 1H), 1.65–2.4 (m, 5H).

EXAMPLE 12
2-Carbomethoxy-3-(4-tributyltinphenyl)-8-oxabicyclo (3.2.1)-2-octene.

2-Carbomethoxy-3-(4-bromophenyl)-8-oxabicyclo{3.2.1}-2-octene (200 mg, 0.62 mmol), bis(tributyltin) (0.74 mL, 1.46 mmol) and tetrakis(triphenylphosphine)palladium(0) (13 mg, 0.011 mmol) in toluene (4 mL) was degassed by bubbling N$_2$ through the solution for 10 min. The mixture was then heated at reflux for 6 h. Methylene chloride (10 mL) was added and filtered through celite. The filtrate was concentrated to dryness. The residue was purified by flash chromatography and preparative TLC to afford 206 mg (62%) of 2-carbomethoxy-3-(4-tributyltinphenyl)-8-oxabicyclo(3.2.1)-2-octene as a clear viscous oil.

$^1$H NMR (CDCl$_3$, 100 MHz): δ 7.0–7.5 (q, 4H), 5.00 (bm, 1H), 4.65 (t, 1H), 3.50 (s, 3H), 2.98 (dd, 1H), 0.7–2.3 (m, 32H).

EXAMPLE 13
2-Carbomethoxy-3-(4-iodophenyl)-8-oxabicyclo(3.2.1)-2-octene.

2-Carbomethoxy-3-(4-tributyltinphenyl)-8-oxabicyclo (3.2.1)-2-octene (206 mg, 0.39 mmol) in THF (anhydrous, 5 mL) was degassed by bubbling N$_2$ for 10 min. N-Iodosuccinimide (96 mg, 0.43 mmol) was added. The reaction mixture was stirred at room temperature for 1 h and concentrated to dryness. The residue was dissolved in ether (10 mL), washed with saturated NaHCO$_3$ and brine. The dried (MgSo$_4$) ether layer was concentrated to dryness. The residue was purified by flash chromatography and preparative TLC to afford 128 mg (90%) of 2-carbomethoxy-3-(4-iodophenyl)-8-oxabicyclo(3.2.1)-2-octene as a pale yellow viscous oil.

$^1$H NMR (CDCl$_3$, 100 MHz): δ 6.75–7.80 (q, 4H), 5.00 (bm, 1H), 4.64 (t, 1H), 3.54 (s, 3H), 2.95 (dd, 1H), 1.55–2.40 (m, 5H).

EXAMPLE 14
2β-Carbomethoxy-3α-(4-bromophenyl)-8-oxabicyclo (3.2.1)octane
and
2β-Carbomethoxy-3β-(4-bromophenyl)-8-oxabicyclo (3.2.1)octane.

Reaction of 2-carbomethoxy-3-(4-bromophenyl)-8-oxabicyclo(3.2.1)-2-octene (173 mg, 0.54 mmol) in THF (3 mL) and SmI$_2$ (0.1 M solution in THF, 24 mL, 2.4 mmol), as described above, gave 81 mg (47%) of 2β-carbomethoxy-3α-(4-bromophenyl)-8-oxabicyclo(3.2.1)octane as a white solid, mp. 96–98° C. and 56 mg (32%) of 2β-carbomethoxy-3β-(4-bromophenyl)-8-oxabicyclo(3.2.1)-octane as a white solid, mp. 113–115° C.

$^1$H NMR (CDCl$_3$, 0 MHz) (2β-Carbomethoxy-3α-(4-bromophenyl)-8-oxabicyclo(3.2.1)octane): δ 7.0–7.6 (q, 4H), 4.50 (bd, 2H), 3.60 (s, 3H), 3.25 (dt, 1H), 1.1–2.6 (m, 7H).

$^1$H NMR (CDCl$_3$, 100 MHz) (2β-Carbomethoxy-3β-(4-bromophenyl)-8-oxabicyclo(3.2.1)octane): δ 7.0–7.6 (m, 4H), 4.70 (m, 2H), 3.53 ml(s, 3H), 3.20 (dt, 1H), 2.55–2.92 (m, 2H), 1.5–2.3 (m, 5H).

EXAMPLE 15
2β-Carbomethoxy-3α-(4-tributyltinphenyl)-8-oxabicyclo (3.2.1)octane.

2β-Carbomethoxy-3α-(4-bromophenyl)-8-oxabicyclo (3.2.1)octane (220 mg, 0.68 mmol), bis(tributyltin) (0.8 mL,) tetrakis(triphenylphosphine)palladium(0) (26 mg) and toluene (3 mL) were combined and degassed for 10 min. The reaction mixture was heated at reflux for 2 h. CH$_2$Cl$_2$ (10 mL) was added and filtered through celite. The filtrate was concentrated to dryness. The residue was purified by flash chromatography and preparative TLC to afford 147 mg (41%) of 2β-carbomethoxy-3α-(4-tributyltinphenyl)-8-oxabicyclo(3.2.1)octane as clear viscous oil.

$^1$H NMR (CDCl$_3$, 100 MHz): δ 7.1–7.5 (q, 4H), 4.35–4.65 (bd, 2H) 3.60 (s, 3H), 3.25 (dt, 1H), 0.7–2.65 (m, 34H).

EXAMPLE 16
2β-Carbomethoxy-3α-(4-iodophenyl)-8-oxabicyclo(3.2.1) octane.

2β-Carbomethoxy-3α-(4-tributyltinphenyl)-8-oxabicyclo (3.2.1)octane (147 mg, 0.275 mmol) and THF (3 mL) was degassed for 10 min. N-Iodosuccinimide (63 mg, 0.28 mmol) was added. The reaction mixture was stirred at room temperature for 30 min. After concentration to dryness, the residue was dissolved in ether (50 mL) and washed with saturated NaHCO$_3$, H$_2$O and brine. The dry (Na$_2$SO$_4$) ether layer was concentrated to dryness. The residue was purified by flash chromatography to afford 87 mg (85%) of 2β-carbomethoxy-3α-(4-iodophenyl)-8-oxabicyclo(3.2.1) octane as a white solid, mp. 124–126° C.

$^1$H NMR (CDCl$_3$, 100 MHz): δ 6.8–7.7 (q, 4H), 4.3–4.7 (bd, 2H), 3.6 (s, 3H), 3.2 (dt, 1H), 1.1–2.6 (m, 7H).

EXAMPLE 17
2β-Carbomethoxy-3β-(4-nitrophenyl)-8-oxabicyclo(3.2.1) octane.

To 2β-carbomethoxy-3β-phenyl-8-oxabicyclo(3.2.1) octane (112 mg, 0.45 mmol) in CH$_3$CN (anhydrous, 5 mL) at −5° C. was added NO$_2$BF$_4$ (83 mg, 0.63 mmol). The reaction mixture was stirred at −5° C. for 3 h. A small amount of ice was added and stirred at −25° C. of 15 min. The CH$_3$CN was removed, the melted ice was extracted with ether. The combined ether extract and CH$_3$CN solution was concentrated to dryness. The residue was dissolved in ether (50 mL), washed with saturated NaHCO$_3$ and brine. The dried (MgSO$_4$) ether layer was concentrated to dryness. The residue was purified by flash chromatography to afford 75.6 mg (57%) of 2β-carbomethoxy-3β-(4-nitrophenyl)-8-oxabicyclo(3.2.1)octane.

$^1$H NMR (CDCl$_3$, 100 MHz): δ 7.35–8.3 (q, 4H), 4.75 (bt, 2H), 3.54 (s, 3H), 3.3 (m, 1H), 2.6–3.0 (m, 2H), 1.7–2.4 (m, 5H).

EXAMPLE 18
2β-Carbomethoxy-3β-(4-aminophenyl)-8-oxabicyclo(3.2.1) octane.

2β-Carbomethoxy-3β-(4-nitrophenyl)-8-oxabicyclo (3.2.1)octane (75.6 mg, 0.026 mmol) in MeOH (20 mL) was hydrogenated overnight at room temperature using Raney Ni as catalyst. The reaction mixture was filtered through celite, washed with MeOH and concentrated to dryness. The residue was purified by flash chromatography to afford 43 mg (75%) of 2β-carbomethoxy-3β-(4-aminophenyl)-8-oxabicyclo(3.2.1)octane.

$^1$H NMR (CDCl$_3$, 100 MHz): δ 6.5–7.2 (q, 4H), 4.65 (bd, 2H), 3.58 (s, 1H), 3.50 (s, 3H), 3.1 (m, 1H), 2.5–2.9 (m, 2H), 1.42–2.32 (m, 6H).

EXAMPLE 19
2β-Carbomethoxy-3β-(4-iodophenyl)-8-oxabicyclo(3.2.1) octane.

To 2β-carbomethoxy-3β-(4-aminophenyl)-8-oxabicyclo (3.2.1)octane (26 mg, 0.099 mmol) in $CH_2I_2$ (2 mL) under $N_2$ was added isoamylnitrite (0.17 mL, 0.126 mmol). The reaction mixture was stirred at room temperature for 1 h then at 55° C. for 3 h. $CH_2I_2$ was removed under reduced pressure. The residue was purified by flashed chromatography to afford 15 mg (41%) of 2β-carbomethoxy-3β-(4-iodophenyl)-8-oxabicyclo(3.2.1)octane as a white solid, mp 119–120.5° C.

$^1$H NMR ($CDCl_3$, 100 MHz): δ 6.90–7.80 (q, 4H), 4.65 (bd, 2H), 3.52 (s, 3H), 3.0–3.3 (m, 1H), 2.5–2.9 (m, 2H), 1.6–2.3 (m, 5H).

EXAMPLE 20
2-Carbomethoxy-3-hydroxy-8-oxabicyclo(3.2.1)octane.

$NaBH_4$ (2.56 g, 67.7 mmol) was added to a solution of 2-carbomethoxy-8-oxabicyclo(3.2.1)octan-3-one, 3, (5.12 g, 27.8 mmol) in MeOH (100 mL) at −78° C. The reaction mixture was left at room temperature overnight. The solution was concentrated to dryness. The residue was dissolved in water (50 mL), and extracted with $CH_2Cl_2$ (100, 2×50 mL). The combined dried ($MgSO_4$) extracts were concentrated to dryness (yield: 3.9 g). By repeated flash column chromatography four isomers were obtained from the residue (2.9 g). The major isomer was 2α-carbomethoxy-3α-hydroxy-8-oxabicyclo(3.2.1)octane (1.0 g, 26%). Some of the other isomers were isolated to be used in the following reactions but there were still mixed fractions. Other pure isomers obtained:

2β-carbomethoxy-3α-hydroxy-8-oxabicyclo(3.2.1) octane (28 mg),

2β-carbomethoxy-3β-hydroxy-8-oxabicyclo(3.2.1)octane (305 mg) and

2α-carbomethoxy-3β-hydroxy-8-oxabicyclo(3.2.1) octane (84 mg).

$^1$H NMR ($CDCl_3$, 100 MHz): (2β,3α) δ 4.75 (bd, 1H), 4.4 (bt, 2H), 3.75 (s, 3H), 2.55 (s, 1H), 1.8–2.5 (m, 7H); (2β,3β) δ 4.8 (bd, 1H), 4.45 (bs, 1H), 3.8–4.15 (m, 1H), 3.78 (s, 3H), 2.8 (d, 1H), 1.6–2.1 (m, 7H); (2α,3α) δ 4.65 (bq, 1H), 4.4 (bs, 2H), 3.78 (s, 3H), 3.45 (s, 1H), 2.95 (t, 1H), 1.8–2.4 (m, 6H); (2α,3β) δ 4.62 (bq, 1H), 4.5 (bs, 1H), 4.2 (dt,1H), 3.75 (s, 3H), 2.68 (dd, 2H), 1.5–2.1 (m, 6H).

EXAMPLE 21
2β-Carbomethoxy-3α-hydroxy-8-oxabicyclo(3.2.1)octane.

2α-Carbomethoxy-3α-hydroxy-8-oxabicyclo(3.2.1) octane (397 mg, 2.1 mmol) and saturated $NaHCO_3$ (10 mL) were combined and heated overnight at reflux. Water was removed. Methanolic HCl (10 mL) was added and stirred at room temperature overnight. The reaction mixture was concentrated to dryness. $CH_2Cl_2$ (25 mL) was added to the residue. The dried ($K_2CO_3$) $CH_2Cl_2$ solution was concentrated to dryness. The residue was chromatographed with silica gel (30% EtOAc/hexanes) to afford 82 mg (21%) of 2β-carbomethoxy-3α-hydroxy-8-oxabicyclo(3.2.1)octane.

$^1$H NMR ($CDCl_3$, 100 MHz): δ 4.75 (bd, 1H), 4.4 (bt, 2H), 3.75 (s, 3H), 2.55 (s, 1H), 1.8–2.5 (m, 7H).

EXAMPLE 22
2β-Carbomethoxy-3α-{bis(4-fluorophenyl)methoxy}-8-oxabicyclo(3.2.1)octane 2β-Carbomethoxy-3α-hydroxy-8-oxabicyclo(3.2.1) octane (103 mg, 0.55 mmol), 4,4'-difluorobenzhydrol (244 mg, 1.1 mmol), p-toluenesulfonic acid monohydrate (60 mg, 0.31 mmol) and benzene (50 mL) in a 100 mL round bottom flask fitted with Dean-Stark trap and condenser was heated overnight at reflux. The reaction mixture was cooled to room temperature and basified with $NH_4OH$. EtOAc (25 mL) was added and washed with brine. The dried ($MgSO_4$) organic layer was concentrated to dryness. The residue was purified by flash chromatography to afford 200 mg (93%) 2β-carbomethoxy-3α-{bis(4-fluorophenyl)methoxy}-8-oxabicyclo(3.2.1)octane as a white solid, mp. 92–93° C.

$^1$H NMR ($CDCl_3$, 100 MHz): δ 6.9–7.5 (m, 8H), 5.38 (s, 1H), 4.75 (bd, 1H), 4.4 (bt, 1H), 4.05 (bd, 1H), 3.70 (s, 3H), 2.65 (s, 1H), 1.6–2.5 (m, 6H).

EXAMPLE 23
2β-Carbomethoxy-3β-{bis(4-fluorophenyl)methoxy}-8-oxabicyclo(3.2.1)octane Reaction of 2β-carbomethoxy-3β-hydroxy-8-oxabicyclo (3.2.1)octane (103 mg, 0.55 mmol), 4,4'-difluorobenzhydrol (244 mg, 1.1 mmol), p-toluenesulfonic acid monohydrate (60 mg, 0.31 mmol) and benzene (50 mL) as above gave 127 mg (59%) of 2β-carbomethoxy-3β-{bis(4-fluorophenyl)methoxy}-8-oxabicyclo(3.2.1)octane as a white solid mp.149–151° C.

$^1$H NMR ($CDCl_3$, 100 MHz): δ 6.85–7.40 (m, 8H), 5.45 (s, 1H), 4.55 (bd, 2H), 3.80 (m, 1H), 3.68 (s, 3H), 2.82 (d, 1H), 2.45 (td, 1H), 1.4–2.1 (m, 5H).

EXAMPLE 24
2α-Carbomethoxy-3α-{bis(4-fluorophenyl)methoxy}-8-oxabicyclo(3.2.1)octane Reaction of 2α-carbomethoxy-3α-hydroxy-8-oxabicyclo (3.2.1)octane (110 mg, 0.59 mmol), 4,4'-difluorobenzhydrol (260 mg, 1.18 mmol), p-toluenesulfonic acid monohydrate (171 mg, 0.89 mmol) and benzene (50 mL), as above, gave 105 mg (46%) of 2α-carbomethoxy-3α-{bis(4-fluorophenyl)-methoxy}-8-oxabicyclo(3.2.1)octane as a light brown gum.

$^1$H NMR ($CDCl_3$, 100 MHz): δ 6.8–7.4 (m, 8H), 5.35 (s, 1H), 4.55 (m, 1H), 4.30 (bs, 1H), 4.15 (bs, 1H), 3.50 (s, 3H), 2.97 (t, 1H), 2.68 (q, 1H), 1.6–2.3 (m, 5H).

EXAMPLE 25
2α-Carbomethoxy-3β-{bis(4-fluorophenyl)methoxy}-8-oxabicyclo(3.2.1)octane Reaction of 2α-carbomethoxy-3β-hydroxy-8-oxabicyclo (3.2.1)octane (84 mg, 0.45 mmol), 4,4'-difluoro-benzhydrol (199 mg, 0.9 mmol), p-toluenesulfonic acid monohydrate (130 mg, 0.68 mmol) and benzene (50 mL), as above, gave 99 mg (57%) of 2α-carbomethoxy-3β-{bis(4-fluorophenyl) methoxy}-8-oxabicyclo(3.2.1)octane as a pale yellow gum.

$^1$H NMR ($CDCl_3$, 100 MHz) δ 6.85–7.40 (m, 8H), 5.50 (s, 1H), 4.40 (m, 2H), 4.05 (dt, 1H), 3.68 (s, 3H), 2.91 (dd, 1H), 1.40–2.10 (m, 6H).

EXAMPLE 26
2-Carbomethoxy-3-(3,4-dichlorphenyl)-8-oxabicylo(3.2.1) oct-3-ene;

2-Carbomethoxy-3-(3,4-dichlorophenyl)-8-oxabicyclo [3.2.1.]oct-2-ene (285 mg, 0.91 mmol), THF/MeOH/$H_2O$ (2 mL/0.67 mL/0.67 ml) and LiOH (139 mg, 3.23 mmol) were combined and stirred overnight at room temperature. Water (20 mL) and ether (10 mL) were added to the reaction mixture. The aqueous layer was acidified with 1N HCl and extracted with ether. The ether layer was washed with brine. The dried ($MgSO_4$) ether layer was concentrated to dryness. The residue was purified by flash chromatography (50% EtOAc/hexane+1% formic acid) to afford 95 mg of the 3-ene-acid (used with no further purification).

3-Ene-acid from above (95 mg, 0.32 mmol), MeOH (10 mL) and thionyl chloride (10 drops) were combined and stirred overnight at room temperature. The reaction mixture was concentrated to dryness. The residue was purified by flash chromatography (10–20% EtOAc/hexanes) to afford 94 mg of 2-carbomethoxy-3-(3,4-dichlorphenyl)-8-oxabicyclo[3.2.1.]oct-3-ene as a white solid: mp 127–128° C. $R_f$ 0.26 (30% EtOAc/hexanes). $^1$H NMR (CDCl$_3$, 100 MHz) 7.1–7.5 (m, 3H), 6.4 (d, 1H), 4.8–5.1 (bd, 1H), 4.6–4.8 (bt, 1H), 3.65 (s, 3H), 3.2 (s, 1H), 1.6–2.5 (m, 4H).

EXAMPLE 27
6(7)-Hydroxy-2-methoxycarbonyl-8-azabicyclo(3.2.1)octane-2-one;
and
6(7)-methoxy-2-methoxycarbonyl-8-azabicyclo(3.2.1)octane-2-one;

To a solution of 60 ml of acetic acid and 43 ml of acetic anhydride at 0° C., was added slowly 40 g (0.27 mol) of acetonedicarboxylic acid. The mixture was stirred and the temperature was not allowed to rise above 10° C. The acid was dissolved slowly and a pale yellow precipitate formed. After 3 h the product was filtered, washed with 30 ml of glacial acetic acid and 100 ml of benzene. The white powder obtained was dried at high vacuum to afford 30 g of acetonedicarboxylic acid anhydride (yield 86%). Mp 137–138° C.

To a flask containing 50 g (0.39 mol) of acetonedicarboxylic acid anhydride was added 160 ml of cold dry MeOH. The monomethylester solution was allowed to stand for 1 h and filtered. The filtrate of acetonedicarboxylic acid monomethyl ester was used directly in the following condensation reaction.

To a 3 L flask with 53.6 g (0.41 mol) of 2,5-dimethoxydihydrofuran was added 1000 ml of 3N HCl solution. The mixture was left to stand for 12 h at room temperature and then neutralized with ice-cold NaOH solution (equal moles) at 0° C. To this red solution, was added 41.3 g (0.62 mol) of methylamine hydrochloride in 300 ml H$_2$O, the preformed methanol solution of the monomethylester (50 g (0.39 mol) of acetone dicarboxylic acid anhydride in 160 ml of methanol) and 50 g of sodium acetate in 200 mL of H$_2$O. The mixture (pH 4.5) was stirred for 2 days and the acidity decreased to pH 4.9. The red solution was extracted with hexane (450 ml×2) to remove nonpolar by-products. The aqueous solution was basified first with NaOH (1N) to neutral pH, then with potassium carbonate. Sodium chloride (about 200 g) was added. The saturated solution was extracted with CH$_2$Cl$_2$ (250 ml×8), then with a mixed solvent (t-butyl:1,2-dichloroethane, 37:63, 250 ml×8). The CH$_2$Cl$_2$ extracted was dried over K$_2$CO$_3$ and solvent was removed to provide 19.6 g of a crude mixture which was separated by column chromatography (SiO$_2$, 10% Et$_3$N, 30–90% EtOAc in hexane and 10% methanol in EtOAc) to afford 7.5 g of 6(7)-methoxy-2-methoxycarbonyl-8-azabicyclo(3.2.1)octane-2-one as an oil and 7 g of 6(7)-hydroxy-2-methoxycarbonyl-8-azabicyclo-(3.2.1)octane-2-one as a crystalline solid.

The mixed solvent extracts were dried and removed in vacuo to afford a pale yellow solid 19.2 g: 6(7)-hydroxy-2-methoxycarbonyl-8-azabicyclo(3.2.1)octane-2-one. The hydroxy tropanones were used without further purification.

$^1$H NMR (CDCl$_3$, 100 MHz): 4.05 (m, 2H, -H), 3.7 (2s, 6H, OCH$_3$), 3.85 (m, 1H), 3.65(1H), 3.45(2H), 3.2(1H), 2.45 (6H), 2.8–1.0 (m, 10H).
7-Methoxy-2-methoxycarbonyl-8-azabicyclo(3.2.1)octane-2-one.

$^1$H NMR (CDCl$_3$, 100 MHz): 12–11.5 (bs, 1H), 3.9 (s, 2H), 3.8 (2s, 6H), 3.67 (s, 2H), 3.65–3.2 (m, 4H), 3.34 (2S, 6H), 2.8–2.6 (m, 4H), 2.82–2.6(m, 4H), 2.4 (s, 6H), 2.25–1.5 (m, 6H). enol:keto (1:1).

EXAMPLE 28
6(7)-Methoxymethoxy-2-methoxycarbonyl-8-azabicyclo (3.2.1)octane-2-ones To a solution of 6(7)-hydroxy-2-methoxycarbonyl-8-azabicyclo(3.2.1)octane-2-one (18 g, 84.5 mmol) in 200 ml of CH$_2$Cl$_2$, 70 ml of dimethoxymethane was added, followed by (18 g, 93 mmol) of p-toluene sulfonic acid monohydrate. The round-bottom flask was fitted with a soxhlet extractor containing 3–4 A molecular sieves. The reaction mixture was heated to reflux with stirring until the starting material had disappeared (TLC). The mixture was cooled and treated with sat. sodium bicarbonate solution and extracted with CH$_2$Cl$_2$. The combined organics were dried over K$_2$CO$_3$ removed in vacuo and applied to column (silica gel, 10% Et$_3$N, 30% EtOAc/hexane). 6-Methoxymethoxy-2-methoxycarbonyl-8-azabicyclo(3.2.1)octane-2-one (2.2 g) was obtained as a yellow oil. $R_f$ 0.3 (10% Et$_3$N, 30% EtOAc in hexane).

$^1$H NMR (CDCl$_3$, 100 MHz): 11.7 (s), 4.64 (2s), 3.76(s), 3.74(s), 3.36(s), 3.35(s), 2.69(s), 2.62(s), 2.41 (s), 4.1–1.8 (m). Enol:keto (1:2).

4.34 g of 7-Methoxymethoxy-2-methoxycarbonyl-8-azabicyclo-(3.2.1)octane-2-one was obtained as a yellow oil. $R_f$ 0.38 (10% Et$_3$N, 30% EtOAc in hexane).

$^1$H NMR (CDCl$_3$, 100 MHz): 11.75 (s), 4.67–4.58 (m), 3.81 (S), 3.79(s), 3.39 (s), 3.37 (s), 2.66 (s), 2.60 (s), 2.42 (s), 4.1–1.8 (m).

A mixture of the (3.2.1)octane-2-ones (2.37 g) and starting material (4.8 g) were obtained from chromatography. Yield 56% based on recovered starting material.

EXAMPLE 29
2-Carbomethoxy-3-trifluoromethylsulfonyloxy-7-methoxymethoxy-8-azabicyclo(3.2.1)-2-octene To a solution of 2-carbomethoxy-7-methoxymethoxy-8-azabicyclo(3.2.1)octanone (4.25 g, 16.5 mmol) in THF (150 mL), sodium bistrimethylsilylamide (1.0M solution in THF, 25 mL) was added dropwise at −70° C. under nitrogen. After stirring for 30 min, N-phenyltrifluoromethanesulfonimide (7.06 g, 19.8 mmol) was added in one portion at −70° C. The reaction was allowed to warm up to room temperature and was stirred overnight. The volatiles were removed on rotary evaporator. The residue was dissolved in CH$_2$Cl$_2$ (200 mL), washed with H$_2$O (100 mL) and brine (100 mL). The dried (MgSO$_4$) CH$_2$Cl$_2$ layer was concentrated to dryness. The residue was purified by flash chromatography (10% Et$_3$N, 20% EtOAc/hexanes) to afford 3.63 g (65%) of 2-carbomethoxy-3-trifluoromethylsulfonyloxy-7-methoxymethoxy-8-axabicyclo(3.2.1)-2-octene as a pale yellow oil.

$^1$H NMR (CDCL$_3$, 100 MHz): 4.69 (m, 2H), 4.21 (dd, 1H), 4.0 (s, 3H), 3.84 (s, 3H), 3.53 (m, 1H), 3.37 (s, 3H), 2.85 (dd, 1H), 2.45 (s, 3H), 2.4–1.8 (m, 3H).

$^{13}$C NMR (CDCL$_3$, 100 MHz): 163.5, 149.5, 124.5, 120.9, 996.1, 95.3, 81.5, 64.9, 56.5, 55.6, 55.3, 52.2, 39.9, 33.9, 33.7, 30.5.

HRMS Calc. (M+1): 390.0856; Found 390.0811.

EXAMPLE 30
2-Carbomethoxy-3-(trifluoromethyl)sulfonyloxy-6-methoxymethoxy-8-axabicyclo(3.2.1)-2-octene The procedure described above in Example 29 was utilized to obtain the product (64%).

$^1$H NMR (CDCL$_3$, 100 MHz): 4.64 (s, 2H), 4.07 (dd, 1H), 3.81 (s, 3H), 3.5–3.30(m, 2H), 3.36 (s, 3H), 2.85 (dd, 1H), 2.44 (s, 3H), 2.4–1.8 (m, 3H).

EXAMPLE 31
2-Carbomethoxy-3-trifluoromethylsulfonyloxy-7-methoxy-8-azabicyclo(3.2.1)-2-octene To a round bottom flask containing 1.1 g of 2-carbomethoxy-7-methoxy-8-azabicyclo(3.2.1)-octane-2-one and 3 ml of $Et_3N$ in 25 ml of $CH_2Cl_2$ (anhydrous), 1.22 ml (7.2 mmol) of triflic anhydride was added drop wise at 0° C. The mixture was allowed to warm up to room temperature and was stirred overnight. The solvent was removed and $NaHCO_3$ (sat.) was added. The mixture was extracted by $CH_2Cl_2$. The organics were combined and dried ($K_2CO_3$), removed in vacuo and the product separated by column chromatography ($SiO_2$, 10% $Et_3N$, 30% EtOAc, 60% hexane).

$^1H$ NMR ($CDCl_3$, 100 MHz): 4.6 ????

General Procedures for Coupling Reactions

To a round-bottom flask with 2-carbomethoxy-3-{[(trifluoromethyl)sulfonyl]oxy}-7-methoxymethoxy-8-oxabicyclo(3.2.1)-2-octene (1 eq), LiCl (2 eq), and tris (dibenzylideneacetone)dipalladium(0) (5% molecular eq) in diethoxymethane (10 mL), and $Na_2CO_3$ (2M solution, 2 eq), was added 3,4-dichlorophenyl boronic acid (1.3 eq). The mixture was heated to reflux until the starting material disappeared (TLC). The mixture was cooled to room temperature, filtered through celite and washed with ether (100 mL). The mixture was basified with $NH_4OH$ and washed with brine. The dried ($MgSO_4$) ether layer was concentrated to dryness. The residue was purified by flash chromatography (10% $Et_3N$, 30% EtOAc, 60% hexane) to afford tropene as a light yellow oil.

EXAMPLE 32
2-Carbomethoxy-3-(3,4-dichlorophenyl)-7-methoxymethoxy-8-azabicyclo(3.2.1)-2-octene The above general procedure for coupling reactions provided the product in 80% yield. $R_f$ 0.29 (10% $Et_3N$, 30% EtOAc, 60% hexane).

$^1H$ NMR ($CDCl_3$, 100 MHz): 7.40(d, 1H), 7.19(d, 1H), 6.93(dd, 1H), 4.71(AB, 2H), 4.24 (dd, 1H), 3.91 (s, 1H), 3.56 (s, 3H), 3.48 (b, 1H), 3.39 (s, 3H), 2.52 (s, 3H), 2.90–1.5.(m, 4H).

$^{13}C$ NMR ($CDCl_3$, 100 MHz): 168.3, 144.8, 142.0, 133.4, 132.8, 131.3, 129.9, 128.2, 127.4, 96.4, 83.2, 66.3, 57.5, 56.5, 52.7, 41.5, 36.0, 35.7.

EXAMPLE 33
2-Carbomethoxy-3-(4-fluorophenyl)-7-methoxymethoxy-8-azabicyclo(3.2.1)-2-octene The above general procedure for coupling reactions provided the product.

$^1H$ NMR ($CDCl_3$, 100 MHz): 6.99–7.12 (m, 4H), 5.00 (bm, 2H), 4.64 (t, 1H), 3.52 (s, 3H), 2.95 (dd, 1H), 1.71–2.19 (m, 5H).

EXAMPLE 34
2-Carbomethoxy-3-(3,4-dichlorophenyl)-7-methoxy-8-azabicyclo(3.2.1)-2-octene The above general procedure for coupling reactions provided the product in 76% yield. $R_f$ 0.29 (10% $Et_3N$, 30% EtOAc, 60% hexane).

$^1H$ NMR ($CDCl_3$, 100 MHz): 7.38 (d, 1H), 7.23 (d, 1H), 6.94 (dd, 1H), 3.95 (s, 1H), 3.87 (dd, 1H), 3.56 (s, 3H), 3.39 (s, 3H), 2.70 (dd, 1H), 2.49 (s, 3H), 2.40–1.6 (m, 4H).

EXAMPLE 35
2-Carbomethoxy-3-(4-fluorophenyl)-7-methoxy-8-azabicyclo(3.2.1)-2-octene The above general procedure for coupling reactions provided the product in 70% yield. $R_f$ 0.37 (10% $Et_3N$, 30% EtOAc, 60% hexane).

$^1H$ NMR ($CDCl_3$, 100 MHz): 7.08–7.0 (m, 4H), 3.94 (bs, 1H), 3.80 (dd, 1H), 3.53 (s, 3H), 3.39 (s, 3H), 2.76 (dd, 1H), 2.50 (s, 3H), 2.2–1.6 (m, 5H).

General Procedures for SmI$_2$ Reduction Reactions

To a THF solution of 2-carbomethoxy-3-aryl-6(7)-methoxymethoxy-8-azabicyclo(3.2.1)-2-octene (1 eq) with anhydrous methanol (20 eq) at −78° C. under $N_2$ was added $SmI_2$ (0.1 M solution in THF, 10 eq). The mixture was stirred at −78° C. for 4 h and then quenched with $H_2O$ (10 mL). After warming to room temperature, $NaHCO_3$ (sat.) was added and the mixture was filtered through celite and washed with ether (400 mL). The ether layer was washed with brine. The dried ($MgSO_4$) ether layer was concentrated to dryness. The isomers were separated by gravity column (2–4% methanol/$CH_2Cl_2$) to afford the boat and chair isomers.

EXAMPLE 36
2β-Carbomethoxy-3-(3,4-dichlorophenyl)-7-methoxymethoxy-8-azabicyclo(3.2.1)octane
and
2β-carbomethoxy-3-(3,4-dichlorophenyl)-7-methoxymethoxy-8-azabicyclo(3.2.1)octane The reaction of 2-carbomethoxy-3-3,4-dichlorophenyl)-7-methoxymethoxy-8-azabicyclo(3.2.1)-2-octene (0.494 g, 1.28 mmol) in THF (10 mL) and $SmI_2$ (0.1 M solution in THF, 128 mL, 12.8 mmol) as described above, gave 196 mg (40%) of 2β-carbomethoxy-3-(3,4-dichlorophenyl)-7-methoxymethoxy-8-azabicyclo(3.2.1)octane as an oil, and 114 mg (22%) of 2β-carbomethoxy-3β-(3,4-dichlorophenyl)-7-methoxymethoxy-8-azabicyclo(3.2.1) octane as an oil.

$^1H$ NMR ($CDCl_3$, 100 MHz): 7.25 (bs, 5H), 4.51 (bd, 2H), 3.58 (s, 3H), 3.25 (dt, 1H), 2.51 (dd, 1H), 2.38 (m, 1H), 1.6–2.2 (m, 4H), 1.41 (ddd, 1H).

$^1H$ NMR ($CDCl_3$, 100 MHz): 7.25 (bs, 5H), 4.65 (m, 2H), 3.48 (s, 3H), 3.25 (dt, 1H), 2.78 (d, 1H), 2.73 (dt, 1H), 1.5–2.3 (m, 5H).

EXAMPLE 37
2β-Carbomethoxy-3-(fluorophenyl)-7-methoxymethoxy-8-azabicyclo(3.2.1)octane
and
2β-carbomethoxy-3β-(fluorophenyl)-7-methoxymethoxy-8-azabicyclo(3.2.1)octane Reaction of 2-carbomethoxy-3-(fluorophenyl)-7-methoxymethoxy-8-azabicyclo(3.2.1)-2-octene (0.494 g, 1.28 mmol) in THF (10 mL) and $SmI_2$ (0.1 M solution in THF, 128 mL, 12.8 mmol), as described, above gave 196 mg (40%) of 2β-carbomethoxy-3-(fluorophenyl)-7-methoxymethoxy-8-azabicyclo(3.2.1)octane as an oil, and 114 mg (22%) of 2β-carbomethoxy-3β-(fluorophenyl)-7-methoxymethoxy-8-azabicyclo(3.2.1)octane as an oil.

$^1H$ NMR ($CDCl_3$, 100 MHz) (2β-Carbomethoxy-3-(fluorophenyl)-7-methoxymethoxy-8-azabicyclo(3.2.1) octane): 7.3–6.8 (m, 4H), 4.65 (2d, 2H), 4.25 (dd, 1H), 3.60 (s, 3H), 3.38 (s, 3H), 2.55 (s, 3H), 3.5–1.8 (m, 9H).

$^1H$ NMR ($CDCl_3$, 100 MHz) (2β-Carbomethoxy-3β-(fluorophenyl)-7-methoxymethoxy-8-azabicyclo(3.2.1) octane ): 7.3–6.8 (m, 4H), 4.70 (s, 2H), 4.35 (dd, 1H), 3.59

(bs, 1H), 3.50 (s, 3H), 3.42 (s, 3H), 3.0 (m, 1H), 2.6 (m, 1H), 2.48 (s, 3H), 2.5–1.2 (m, 5H).

EXAMPLE 38
2β-Carbomethoxy-3-(3,4-dichlorophenyl)-7-methoxy-8-azabicyclo(3.2.1)octane
and
2β-carbomethoxy-3β-(3,4-dichlorophenyl)-7-methoxy-8-azabicyclo(3.2.1)octane Reaction of 2-carbomethoxy-3-(3,4-dichlorophenyl)-7-methoxy-8-azabicyclo(3.2.1)-2-octene (0.287 g, 0.81 mmol) in THF (10 mL) and $SmI_2$ (0.1 M solution in THF, 81 mL, 8.1 mmol) in 5 mL of methanol as described above gave 123.4 mg (43%) of 2β-carbomethoxy-3-(3,4-dichlorophenyl)-7-methoxy-8-azabicyclo(3.2.1)octane as an oil, and 83 mg (32%) of 2β-carbomethoxy-3β-(3,4-dichlorophenyl)-7-methoxy-8-azabicyclo(3.2.1)octane as an oil.

$^1$H NMR ($CDCl_3$, 100 MHz) (2β-Carbomethoxy-3-(3,4-dichlorophenyl)-7-methoxy-8-azabicyclo(3.2.1)octane): 7.25(bs, 5H), 4.51.

$^1$H NMR ($CDCl_3$, 400 MHz) (2β-Carbomethoxy-3β-(3,4-dichlorophenyl)-7-methoxy-8-azabicyclo(3.2.1)octane): 7.31 (d, J=8.5 Hz, 1H, Ph), 7.28 (d, J=1.8 Hz, 1H, Ph), 7.07 (dd, J=8.5, 1.8 Hz, 1H, Ph), 3.96 (dd, J=7.3, 3.0 Hz, 1H, $H_{7a}$), 3.61 (br s, 1H, $H_1$), 3.52 (br s, 1H, $H_5$), 3.51 (s, 3H, $CO_2Me$), 3.34 (s, 3H, OMe), 2.95 (dd, J=4.6, 3.7 Hz, 1H, $H_{2a}$), 2.64 (ddd, J=9.8, 6.4, 4.6 Hz, 1H, $H_{3a}$), 2.47 (m, 1H, $H_{4b}$), 2.43 (s, 3H, NMe), 2.18 (ddd, J=14.1, 6.7, 3.0 Hz, 1H, $H_{6b}$), 2.10 (dd, J=14.0, 7.3 Hz, 1H, $H_{6a}$), 1.55 (m, 1H, $H_{4a}$).

EXAMPLE 39
2β-Carbomethoxy-3-(fluorophenyl)-7-methoxy-8-azabicyclo(3.2.1)octane
and
2β-Carbomethoxy-3β-(fluorophenyl)-7-methoxy-8-azabicyclo(3.2.1)octane Reaction of 2-carbomethoxy-3-(fluorophenyl)-7-methoxy-8-azabicyclo(3.2.1)-2-octene (0.585 g, 1.92 mmol) in THF (10 mL) and $SmI_2$ (0.1 M solution in THF, 192 mL, 19.2 mmol), as described above, gave 230 mg (40%) of 2β-carbomethoxy-3-(fluorophenyl)-7-methoxy-8-azabicyclo(3.2.1)octane as an oil, and 245 mg (42%) of 2β-carbomethoxy-3β-(fluorophenyl)-7-methoxy-8-azabicyclo(3.2.1)octane as an oil.

$^1$H NMR ($CDCl_3$, 100 MHz) (2β-Carbomethoxy-3-(fluorophenyl)-7-methoxy-8-azabicyclo(3.2.1)octane): 7.3–6.8(m, 4H), 3.86 (dd, 1H), 3.61(s, 3H), 3.38(s, 3H), 2.53 (s, 3H), 3.5–1.8 (m, 9H).

$^1$H NMR ($CDCl_3$, 100 MHz) (2β-Carbomethoxy-3β-(fluorophenyl)-7-methoxy-8-azabicyclo(3.2.1)octane): 7.3–7.0 (m, 4H), 4.70 (s, 2H), 4.35 (dd, 1H), 3.59 (bs, 1H), 3.50 (s, 3H), 3.42 (s, 3H), 3.0 (m, 1H), 2.6 (m, 1H), 2.48 (s, 3H), 2.5–1.2 (m, 5H).

General Procedure for the Deprotection of the MOM Group

To a solution of MOM protected alcohol in $CH_2Cl_2$ (anhyd.) containing 4 Å molecular sieves at 0° C., was added TMSBr (10 eq). The solution was stirred for 1 h at 0° C., then warmed to room temperature. After stirring overnight, $NaHCO_3$ (sat) was added and extracted with $CH_2Cl_2$. The extract was dried ($Na_2CO_3$) and reduced in vacuo to apply to a column (Silica Gel, 10% $Et_3N$, 30–90% EtOAc in hexane). The desired product was obtained as a solid and was dissolved in minimum volume of EtOAc. To this solution ethereal HCl (1M, 1.1 eq) was added dropwise to afford the HCl salt.

EXAMPLE 40
2β-Carbomethoxy-3-(3,4-dichlorophenyl)-7-hydroxy-8-azabicyclo(3.2.1)octane 2β-Carbomethoxy-3-(3,4-dichlorophenyl)-7-methoxymethoxy-8-azabicyclo(3.2.1)octane (49 mg, 0.13 mmol) and TMSBr (0.17 mL, 1.3 mmol) were reacted, as described above. The product was obtained in 87% yield (41 mg). $R_f$ 0.18 (10% $Et_3N$, 40% EtOAc, 50% hexane).

EXAMPLE 41
2β-Carbomethoxy-3β-(3,4-dichlorophenyl)-7-methoxy-8-azabicyclo(3.2.1)octane 2β-Carbomethoxy-3β-(3,4-dichlorophenyl)-7-methoxymethoxy-8-azabicyclo(3.2.1)octane (50 mg, 0.13 mmol) and TMSBr (0.17 mL, 1.3 mmol) were reacted, as described above. The product was obtained in 88% yield (42.1 mg). $R_f$ 0.18 (10% $Et_3N$, 40% EtOAc, 50% hexane).

$^1$H NMR data (400 MHz, $CDCl_3$): (7β-OH) 7.31 (d, J=8.5 Hz, 1H, Ph), 7.27 (d, J=1.8 Hz, 1H, Ph), 7.05 (dd, J=8.5, 1.8 Hz, 1H, Ph), 4.52 (dd, J=6.8, 3.1 Hz, 1H, $H_{7a}$), 3.58 (br s, Biological assays were performed using the following procedures.

A. Tissue Sources and Preparation.

Brain tissue from adult male and female cynomolgus monkeys (*Macaca fascicularis*) is stored at −85° C. in the primate brain bank at the New England Regional Primate Research Center. The caudate-putamen will be dissected from coronal slices and yields 1.4±0.4 g tissue. Membranes are prepared as described previously. Briefly, the caudate-putamen is homogenized in 10 volumes (w/v) of ice-cold Tris.HCl buffer (50 mM, pH 7.4 at 4° C.) and centrifuged at 38,000×g for 20 min in the cold. The resulting pellet is suspended in 40 volumes of buffer, and the entire procedure is repeated twice. The membrane suspension (25 mg original wet weight of tissue/ml) is diluted to 12 ml/ml for $^3$H-WIN 35,428 or $^3$H-citalopram assay in buffer just before assay and is dispersed with a Brinkmann Polytron homogenizer (setting #5) for 15 sec. All experiments are conducted in triplicate and each experiment is repeated in each of 2–3 preparations from individual brains.

TABLE 3

Elemental Analyses

| COMPOUND | CALCULATED | | | FOUND | | |
| --- | --- | --- | --- | --- | --- | --- |
| | C | H | Cl | C | H | Cl |
| (1R,1S)-2-Carbomethoxy-3-phenyl-8-oxabicyclo(3.2.1)-2-octene Anal.($C_{15}H_{16}O_3$) | 73.75 | 6.60 | | 73.72 | 6.65 | |
| (1R,1S)-2-Carbomethoxy-3-(4-fluorophenyl)-8-oxabicyclo(3.2.1)-2-octene | 68.69 | 5.77 | | 68.55 | 5.84 | |

TABLE 3-continued

Elemental Analyses

| COMPOUND | CALCULATED | | | FOUND | | |
|---|---|---|---|---|---|---|
| | C | H | Cl | C | H | Cl |
| Anal.($C_{15}H_{15}O_3F$) (1R,1S)-2-Carbomethoxy-3-(4-chlorophenyl)-8-oxabicyclo(3.2.1)-2-octene Anal.($C_{15}H_{15}O_3Cl$) | 64.63 | 5.42 | 12.72 | 64.56 | 5.46 | 12.65 |
| (1R,1S)-2-Carbomethoxy-3-(4-bromophenyl)-8-oxabicyclo(3.2.1)-2-octene Anal.($C_{15}H_{15}O_3Br$) | 55.74 | 4.68 | Br: 24.72 | 55.46 | 4.70 | Br: 24.49 |
| (1R,1S)-2-Carbomethoxy-3-(4-iodophenyl)-8-oxabicyclo(3.2.1)-2-octene Anal.($C_{15}H_{15}O_{31}I$) | 48.67 | 4.08 | I: 34.28 | 48.91 | 4.21 | I: 34.01 |
| (1R,1S)-2-Carbomethoxy-3-(3,4-dichlorophenyl)-8-oxabicyclo(3.2.1)-2-octene Anal.($C_{15}H_{14}O_3Cl_2$) | 57.53 | 4.51 | 22.64 | 57.39 | 4.54 | 22.50 |
| (1R)-2-Carbomethoxy-3-(3,4-dichlorophenyl)-8-oxabicyclo(3.2.1)-2-octene Anal.($C_{15}H_{14}O_3Cl_2$) | 57.53 | 4.51 | 22.64 | 57.50 | 4.55 | 22.71 |
| (1S)-2-Carbomethoxy-3-(3,4-dichlorophenyl)-8-oxabicyclo(3.2.1)-2-octene Anal.($C_{15}H_{14}O_3Cl_2$) | 57.53 | 4.51 | 22.64 | 57.63 | 4.48 | 22.54 |
| (1R,1S)-2-Carbomethoxy-3-phenyl-8-oxabicyclo(3.2.1)octane Anal.($C_{15}H_{18}O_3$) | 73.14 | 7.37 | | 73.07 | 7.40 | |
| (1R,1S)-2-Carbomethoxy-3-phenyl-8-oxabicyclo(3.2.1)octane Anal.($C_{15}H_{18}O_3$) | 73.14 | 7.37 | | 73.02 | 7.41 | |
| (1R,1S)-2-Carbomethoxy-3(4-fluorophenyl)-8-oxabicyclo(3.2.1)octane Anal.($C_{15}H_{17}O_3F$) | 68.16 | 6.48 | | 67.88 | 6.44 | |
| (1R,1S)-2-Carbomethoxy-3(4-fluorophenyl)-8-oxabicyclo(3.2.1)octane Anal.($C_{15}H_{17}O_3F$) | 68.16 | 6.48 | | 68.10 | 6.52 | |
| (1R,1S)-2-Carbomethoxy-3-(4-chlorophenyl)-8-oxabicyclo(3.2.1)octane Anal.($C_{15}H_{17}O_3Cl$) | 64.17 | 6.10 | 12.63 | 64.01 | 6.09 | 12.51 |
| (1R,1S)-2-Carbomethoxy-3-(4-chlorophenyl)-8-oxabicyclo(3.2.1)octane Anal.($C_{15}H_{17}O_3Cl$) | 64.17 | 6.10 | 12.63 | 64.29 | 6.12 | 12.54 |
| (1R,1S)-2-Carbomethoxy-3(4-bromophenyl)-8-oxabicyclo(3.2.1)octane Anal.($C_{15}H_{17}O_3Br$) | 55.40 | 5.27 | Br: 24.57 | 55.30 | 5.26 | 24.45 |
| (1R,1S)-2-Carbomethoxy-3(4-bromophenyl)-8-oxabicyclo(3.2.1)octane Anal.($C_{15}H_{17}O_3Br$) | 55.40 | 5.27 | Br: 24.57 | 55.49 | 5.29 | Br: 24.63 |
| (1R,1S)-2-Carbomethoxy-3(4-iodophenyl)-8-oxabicyclo(3.2.1)octane Anal.($C_{15}H_{17}O_3I$) | 48.40 | 4.60 | I: 34.10 | 48.55 | 4.66 | I: 34.00 |
| (1R,1S)-2-Carbomethoxy-3-(3,4-dichlorophenyl)-8-oxabicyclo(3.2.1)octane Anal.($C_{15}H_{16}O_3Cl_2$) | 57.16 | 5.12 | 22.50 | 57.18 | 5.19 | 22.61 |
| (1R,1S)-2-Carbomethoxy-3-(3,4-dichlorophenyl)-8-oxabicyclo(3.2.1)octane Anal.($C_{15}H_{16}O_3Cl_2$) | 57.16 | 5.12 | 22.50 | 57.27 | 5.08 | 22.57 |
| (1R)-2-Carbomethoxy-3-(3,4-dichlorophenyl)-8-oxabicyclo(3.2.1)octane Anal.($C_{15}H_{16}O_3Cl_2$) | 57.16 | 5.12 | 22.50 | 57.08 | 5.16 | 22.59 |
| (1R)-2-Carbomethoxy-3-(3,4-dichlorophenyl)-8-oxabicyclo(3.2.1)octane Anal.($C_{15}H_{16}O_3Cl_2$) | 57.16 | 5.12 | 22.50 | 57.27 | 5.18 | 22.57 |
| (1S)-2-Carbomethoxy-3-(3,4-dichlorophenyl)-8-oxabicyclo(3.2.1)octane Anal.($C_{15}H_{16}O_3Cl_2$) | 57.16 | 5.12 | 22.50 | 57.28 | 5.16 | 22.42 |
| (1S)-2-Carbomethoxy-3-(3,4-dichlorophenyl)-8-oxabicyclo(3.2.1)octane Anal.($C_{15}H_{16}O_3Cl_2$) | 57.16 | 5.12 | 22.50 | 57.07 | 5.15 | 22.40 |
| (1R)-2-Carbomethoxy-8-oxabicyclo(3.2.1)octa-2-ene-3-(1'S)-camphanate Anal.($C_{19}H_{24}O_7$) | 62.63 | 6.64 | | 62.72 | 6.64 | |
| (1S)-2-Carbomethoxy-8-oxabicyclo(3.2.1)octa-2-ene-3-(1'R)-camphanate | 62.63 | 6.64 | | 62.72 | 6.64 | |

TABLE 3-continued

Elemental Analyses

| COMPOUND | CALCULATED | | | FOUND | | |
|---|---|---|---|---|---|---|
| | C | H | Cl | C | H | Cl |
| Anal.($C_{19}H_{24}O_7$)<br>(1R,1S)-2 Carbomethoxy-3-[bis(4-fluorophenyl)methoxy]-8-oxabicyclo[3.2.1.]octane | 68.03 | 5.71 | | 68.12 | 5.74 | |
| Anal.($C_{22}H_{22}O_4F_2$)<br>(1R,1S)-2 Carbomethoxy-3-[bis(4-fluorophenyl)methoxy]-8-oxabicyclo[3.2.1.]octane | 68.03 | 5.71 | | 67.92 | 5.68 | |
| Anal.($C_{22}H_{22}O_4F_2$)<br>(1R,1S)-2 Carbomethoxy-3-[bis(4-fluorophenyl)methoxy]-8-oxabicyclo[3.2.1.]octane | 67.00 | 5.79 | | 67.06 | 5.78 | |
| Anal.($C_{22}H_{22}O_4F_2$ ⅓ $H_2O$)<br>(1R,1S)-2 Carbomethoxy-3-[bis(4-fluorophenyl)methoxy]-8-oxabicyclo(3.2.1)octane | 68.03 | 5.71 | | 67.98 | 5.78 | |
| Anal.($C_{22}H_{22}O_4F_2$)<br>2-Carbomethoxy-3-(3,4-dichlorphenyl)-8-oxabicylo(3.2.1)oct-3-ene | 57.53 | 4.51 | 22.64 | 57.58 | 4.52 | 22.54 |
| Anal.($C_{15}H_{14}O_3Cl_2$)<br>7-Methoxymethoxy-2-methoxycarbonyl-8-azabicyclo(3.2.1)octane-2-one | 56.02 | 7.44 | N: 5.44 | 55.99 | 7.41 | N: 5.38 |
| Anal.($C_{12}H_{19}NO_5$)<br>2-Carbomethoxy-3-(3,4-dichiorophenyl)-7-methoxymethoxy-8-azabicyclo(3.2.1)-2-octene | 55.97 | 5.48 | N: 3.63 | 55.89 | 5.54 | N: 3.57 |
| Anal. ($C_{12}H_{19}NO_5$)<br>2-Carbomethoxy-3-(3,4-dichlorophenyl)-7 methoxy-8-azabicyclo(3.2.1)-2-octene | 51.99 | 5.13 | N: 3.57<br>Cl: 27.08 | 51.86 | 5.13 | N: 3.51<br>Cl: 27.19 |
| Anal. ($C_{17}H_{19}ClNO_3HCl$)<br>2-Carbomethoxy-3-(4-fluorophenyl)-7-methoxy-8-azabicyclo(3.2.1)-2-octene | 59.74 | 6.19 | N: 4.10 | 59.48 | 6.23 | N: 4.08 |
| Anal.($C_{12}H_{19}NO_5$)<br>2-carbomethoxy-3-(3,4-dichlorophenyl)-7-methoxymethoxy-8-azabicyclo(3.2.1)octane | 73.14 | 7.37 | | 73.02 | 7.41 | |
| Anal.($C_{15}H_{18}O_3$)<br>2-carbomethoxy-3-(3,4-dichlorophenyl)-7-methoxymethoxy-8-azabicyclo(3.2.1)octane | 73.14 | 7.37 | | 73.07 | 7.40 | |
| Anal.($C_{15}H_{18}O_3$)<br>2-Carbomethoxy-3-(3,4-dichlorophenyl)-7-hydroxy-8-azabicyclo(3.2.1)octane | 48.41 | 5.46 | N: 3.53<br>Cl: 27.69 | 48.42 | 5.29 | N: 3.35<br>Cl: 27.50 |
| Anal.($C_{16}H_{20}Cl_3NO_3$ 0.7$H_2O$)<br>2-Carbomethoxy-3-(3,4-dichlorophenyl)-7-methoxy-8-azabicyclo(3.2.1)octane | 48.41 | 5.46 | N: 3.53<br>Cl: 27.69 | 48.50 | 5.41 | N: 3.35,<br>Cl: 27.50 |
| Anal.($C_{16}H_{20}Cl_3NO_3$ 0.7$H_2O$)<br>2-Carbomethoxy-3-(fluorophenyl)-7-methoxy-8-azabicyclo(3.2.1)octane | 56.15 | 6.99 | N: 3.85 | 56.04 | 6.97 | N: 3.79 |
| Anal.($C_{17}H_{23}ClFNO_3$ 0.11$H_2O$)<br>2-Carbomethoxy-3-(fluorophenyl)-7-methoxy-8-azabicyclo(3.2.1)octane | 56.43 | 6.96 | N: 3.87 | 56.57 | 6.80 | N: 3.83 |
| Anal.($C_{17}H_{23}ClFNO_3$ 0.1$H_2O$)<br>2-Carbomethoxy-3-(3,4-dichlorophenyl)-7-methoxy-8-azabicyclo(3.2.1)octane | 56.99 | 5.91 | N: 3.91<br>Cl: 19.79 | 57.04 | 5.93 | N: 3.97,<br>Cl: 19.86 |
| Anal.($C_{17}H_{21}NCl_2O_3$)<br>2-Carbomethoxy-3-(3,4-dichlorophenyl)-7-methoxy-8-azabicyclo(3.2.1)octane<br>Anal.($C_{17}H_{21}NCl_2O_3$) | 56.99 | 5.91 | N: 3.91<br>Cl: 19.79 | 56.71 | 5.97 | N:3.76,<br>Cl: 20.03 |

B. Dopamine Transporter Assay.

The dopamine transporter is labeled with $^3$H-WIN35,428 (70–85 Ci/mmol, DuPont-NEN). The affinity of novel compounds for the dopamine transporter will be determined in experiments by incubating tissue with a fixed concentration of $^3$H-WIN35,428 and a range of concentration of the compound as previously described {Madras, 1989 #21} Stock solutions are diluted serially in the assay buffer and added (0.2 mL) to the assay medium. The assay tubes receive, in Tris.HCl buffer (50 mM, pH 7.4 at 0–4° C.; NaCl 100 mM), the following constituents at a final assay concentration: drug (0.2 ml; 1 pM–300 pM, depending on affinity), $^3$H-WIN35,428 (0.2 ml; 0.3 or 1 nM); membrane preparation (0.2 ml; 1–4 mg original wet weight of tissue/ml), depending on the assay. The 2 h incubation (0–4° C.) is initiated by addition of membranes and terminated by rapid filtration over Whatman GF/B glass fiber filters pre-soaked in 0.1% bovine serum albumin (Sigma Chem. Co.). The filters are washed twice with 5 ml Tris.HCl buffer (50 mM), incubated overnight at 0–4° C. in scintillation fluor (Beckman Ready-Value, 5 ml) and radioactivity (dpm) is measured by liquid scintillation spectrometry (Beckman 1801). Total binding is defined as $^3$H-WIN35,428 bound in the presence of ineffective concentrations of the drug. Non-specific binding is defined as ³H-WIN35,428 bound in the presence of an excess (30 μM) of (−)-cocaine or mazindol (1 μM). Specific binding is the difference between the two values.

C. Serotonin Transporter Assay.

The serotonin transporter is labeled by ³H-citalopram (spec. act.: 82 Ci/mmol, DuPont-NEN). The serotonin transporter is assayed in caudate-putamen membranes using conditions similar to those for the dopamine transporter. The serotonin transporter is expressed at relatively high density in the caudate-putamen (20 pmol/g) and the affinity of ³H-citalopram is approximately 2 nM. Drug affinities are determined by incubating tissue with a fixed concentration of ³H-citalopram and a range of concentrations of the test compounds. The assay tubes receive, in Tris.HCl buffer (50 mM, pH 7.4 at 0–4° C.; NaCl 100 mM), the following constituents at a final assay concentration: drug (0.2 ml of various concentrations); ³H-citalopram (0.2 ml; 1 nM); membrane preparation (0.2 ml; 4 mg original wet weight of tissue/ml). The 2 h incubation (0–4° C.) is initiated by addition of membranes and terminated by rapid filtration over Whatman GF/B glass fiber filters pre-soaked in 0.1% polyethyleneimine. The filters are washed twice with 5 ml Tris.HCl buffer (50 mM) and the remaining steps are carried out as described above. Total binding is defined as ³H-citalopram bound in the presence of ineffective concentrations of unlabeled citalopram (1 pM) or the test compounds. Non-specific binding is defined as ³H-citalopram bound in the presence of an excess (10 μM) of fluoxetine. Specific binding is the difference between the two values.

D. Norepinephrine Transporter Assay.

The selection of thalamus is based on a previous autoradiographic study reporting this brain region to have high densities of ³H-nisoxetine. The assay conditions for thalamus membranes (Madras 1996) are similar to those for the serotonin transporter. The affinity of ³H-nisoxetine (spec. act.: 74 Ci/mmol, DuPont-NEN) for the norepinephrine transporter is determined in experiments by incubating tissue with a fixed concentration of ³H-nisoxetine and a range of concentrations of unlabeled nisoxetine. The assay tubes receive the following constituents at a final assay concentration: nisoxetine or drug (0.2 ml; 1 pM–300 μM), ³H-nisoxetine (0.2 ml; 0.6 nM); membrane preparation (0.2 ml; 4 mg original wet weight of tissue/ml). The buffer in the assay medium is Tris.HCl: 50 mM, pH 7.4 at 0–4° C.; NaCl 300 mM. The 16 h incubation at 0–4° C. is initiated by addition of membranes and terminated by rapid filtration over Whatman GF/B glass fiber filters pre-soaked in 0.1% polyethyleneimine. The remaining steps are described above. Total binding is defined as ³H-nisoxetine bound in the presencm of ineffective concentrations of drug. Non-specific binding is defined as ³H-nisoxetine bound in the presence of an excess (10 μM) of desipramine. Specific binding is the difference between the two values.

E. Data Analysis.

Data are analyzed by EBDA and LIGAND computer software (Elsevier-Biosoft, UK) Final estimates of IC$_{50}$ and nH values are computed by the EBDA program. Baseline values for the individual drugs are established by computer analysis using the baseline drugs as guide. The LIGAND program provides final parameter estimates of the novel compounds by iterative non-linear curve-fitting and evaluation of one- or two-component binding models.

The present invention has been described in detail, including the preferred embodiments thereof. However, it will be appreciated that those skilled in the art, upon consideration of the present disclosure, may make modifications and/or improvements of this invention and still be within the scope and spirit of this invention as set forth in the following claims.

We claim:

1. A compound having the structural formula:

I.

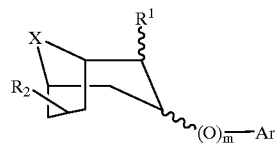

II.

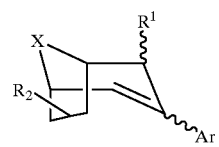

III.

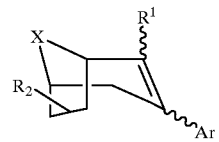

wherein:

$R_1$=COOCH$_3$, COR$_3$, lower alkyl, lower alkenyl, lower alkynyl, CONHR$_4$, or COR$_6$;

$R_2$=is a 6α, 6β, 7α or 7β substituent, which can be selected from OH, OR$_3$, F, Cl, Br, and NHR$_3$;

X=NR$_3$, or NSO$_2$R$_3$;

$R_3$=H, CH$_3$, CH$_3$CH$_2$, CH$_3$(CH$_2$)$_n$ (CH$_2$)$_n$C$_6$H$_4$Y, C$_6$H$_4$Y, CHCH$_2$, lower alkyl, lower alkenyl, or lower alkynyl;

Y=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

$R_4$=CH$_3$, CH$_2$CH$_3$, or CH$_3$SO$_2$;

Ar=phenyl-R$_5$, naphthyl-R$_5$, anthracenyl-R$_5$, phenanthrenyl-R$_5$, or diphenylmethoxy-R$_5$;

$R_5$=Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

$R_6$=morpholinyl or piperidinyl;

m=0 or 1; and n=0, 1, 2, 3, 4 or 5;

when X=N, $R_1$ is not COR$_6$.

2. The compound of claim 1 having the following structural formula:

IV.

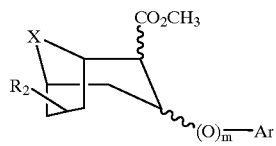

wherein X, Ar, $R_2$ and m have the same meaning as defined above.

3. The compound of claim 2, wherein X is N, $R_2$ is hydroxy or methoxy, and Ar is phenyl, substituted phenyl, diarylmethoxy or substituted diarylmethoxy.

4. The compound of claim 3, wherein Ar is halogen substituted phenyl or halogen substituted diarylmethoxy.

5. The compound of claim 3, wherein Ar is a mono- or di-halogen substituted phenyl.

6. The compound of claim 2, wherein the aryl ring can be substituted with one or more halide atoms, hydroxy groups, nitro groups, amino groups, cyano groups, lower alkyl groups having from 1–8 carbon atoms, lower alkoxy groups having from 1–8 carbon atoms, lower alkenyl groups having from 2–8 carbon atoms, or lower alkynyl groups having from 2–8 carbon atoms.

7. The compound of claim 6, wherein the aryl ring can be substituted with chloride or iodide.

8. The compound of claim 6, wherein the amino group is a mono- or di-alkyl substituted group having from 1–8 carbon atoms.

9. The compound of claim 2, wherein the aryl group has a substituent selected from the group consisting of Br, Cl, I, F, OH, $OCH_3$, $CF_3$, $NO_2$, $NH_2$, CN, $NHCOCH_3$, $N(CH_3)_2$, $COCH_3$, $C(CH_3)_3$, $(CH_2)_nCH_3$ where n=0–6, allyl, isopropyl and isobutyl.

10. The compound of claim 2, wherein the aryl group has a substituent selected from the group consisting of lower alkyl, lower alkenyl and lower alkynyl.

11. The compound of claim 2, wherein the aryl group is substituted with a member of the group consisting of 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH and 3-F-4-OH.

12. The compound of claim 1 having the following structural formula:

VIII.

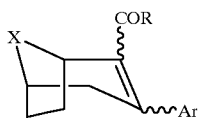

where X is N-alkyl, $R_1$ is morpholinyl, piperidinyl or methoxy, Ar is phenyl, substituted phenyl, naphthyl or substituted naphthyl.

13. The compound of claim 12, wherein Ar is substituted with halogen, lower alkenyl having 2–8 carbon atoms or lower alkynyl having 2–8 carbon atoms.

14. The compound of claim 12, wherein Ar is substituted with 4-Cl, 4-F, 4-Br, 4-I, 3,4-Cl$_2$, ethenyl, propenyl, butenyl, propynyl or butynyl.

15. The compound of claim 1 having the following structural formula:

IX.

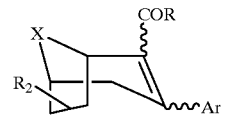

where X is NCH$_3$, $R_1$ is morpholinyl, piperidinyl or methoxy, $R_2$ is hydroxy or methoxy in the 6- or 7-position, Ar is phenyl or naphthyl either of which can be substituted with halogen, alkenyl having 2–8 carbon atoms or alkynyl having 2–8 carbon atoms.

16. The compound of claim 15, wherein Ar is substituted with 4-Cl, 4-F, 4-Br, 4-I, 3,4-Cl$_2$, ethenyl, propenyl, butenyl, propynyl or butynyl.

17. The compound of claim 1 selected from the group consisting of:
  ah. 6-hydroxy-2-methoxycarbonyl-8-azabicyclo(3.2.1)octane-2-one;
  ah. 7-hydroxy-2-methoxycarbonyl-8-azabicyclo(3.2.1)octane-2-one;
  ai. 6-methoxy-2-methoxycarbonyl-8-azabicyclo(3.2.1)octane-2-one;
  aj. 7-methoxy-2-methoxycarbonyl-8-azabicyclo(3.2.1)octane-2-one;
  ak. 6-methoxymethoxy-2-methoxycarbonyl-8-azabicyclo(3.2.1)octane-2-ones;
  al. 7-methoxymethoxy-2-methoxycarbonyl-8-azabicyclo(3.2.1)octane-2-ones;
  am. 2-Carbomethoxy-3-trifluoromethylsulfonyloxy-7-methoxymethoxy-8-azabicyclo(3.2.1)-2-octene;
  an. 2-Carbomethoxy-3-(trifluoromethyl)sulfonyloxy-6-methoxymethoxy-8-azabicyclo(3.2.1)-2-octene;
  ao. 2-Carbomethoxy-3-trifluoromethylsulfonyloxy-7-methoxy-8-azabicyclo(3.2.1)-2-octene;
  ap. 2-Carbomethoxy-3-(3,4-dichlorophenyl)-7-methoxymethoxy-8-azabicyclo(3.2.1)-2-octene;
  aq. 2-Carbomethoxy-3-(4-fluorophenyl)-7-methoxymethoxy-8-azabicyclo(3.2.1)-2-octene;
  ar. 2-Carbomethoxy-3-(3,4-dichlorophenyl)-7-methoxy-8-azabicyclo(3.2.1)-2-octene;
  as. 2-Carbomethoxy-3-(4-fluorophenyl)-7-methoxy-8-azabicyclo(3.2.1)-2-octene;
  at. 2β-Carbomethoxy-3-(3,4-dichlorophenyl)-7-methoxymethoxy-8-azabicyclo(3.2.1)octane;
  au. 2β-carbomethoxy-3-(3,4-dichlorophenyl)-7-methoxymethoxy-8-azabicyclo(3.2.1)octane;
  av. 2β-Carbomethoxy-3-(3,4-dichlorophenyl)-7-methoxymethoxy-8-azabicyclo(3.2.1)octane;
  aw. 2β-carbomethoxy-3-(3,4-dichlorophenyl)-7-methoxymethoxy-8-azabicyclo(3.2.1)octane;
  ax. 2β-Carbomethoxy-3-(3,4-dichlorophenyl)-7-methoxy-8-azabicyclo(3.2.1)octane;
  ay. 2β-carbomethoxy-3β-(3,4-dichlorophenyl)-7-methoxy-8-azabicyclo(3.2.1)octane;
  az. 2β-Carbomethoxy-3-(fluorophenyl)-7-methoxy-8-azabicyclo(3.2.1)octane; and
  aaa. 2β-Carbomethoxy-3β-(fluorophenyl)-7-methoxy-8-azabicyclo(3.2.1)octane.

18. The compound of claim 1 selected from the group consisting of:
  i. 2-Carbomethoxy-3-trifluoromethylsulfonyloxy-7-methoxymethoxy-8-azabicyclo(3.2.1)-2-octene;

j. 2-Carbomethoxy-3-(trifluoromethyl)sulfonyloxy-6-methoxymethoxy-8-axabicyclo(3.2.1)-2-octene;

k. 2-Carbomethoxy-3-trifluoromethylsulfonyloxy-7-methoxy-8-azabicyclo(3.2.1)-2-octene;

l. 2-Carbomethoxy-3-(3,4-dichlorophenyl)-7-methoxymethoxy-8-azabicyclo(3.2.1)-2-octene;

m. 2-Carbomethoxy-3-(4-fluorophenyl)-7-methoxymethoxy-8-azabicyclo(3.2.1)-2-octene;

n. 2-Carbomethoxy-3-(3,4-dichlorophenyl)-7-methoxy-8-azabicyclo(3.2.1)-2-octene; and o. 2-Carbomethoxy-3-(4-fluorophenyl)-7-methoxy-8-azabicyclo(3.2.1)-2-octene.

19. The compound of claim 1 selected from the group consisting of:

a. 6-hydroxy-2-methoxycarbonyl-8-azabicyclo(3.2.1)octane-2-one;

b. 7-hydroxy-2-methoxycarbonyl-8-azabicyclo(3.2.1)octane-2-one;

c. 6-methoxy-2-methoxycarbonyl-8-azabicyclo(3.2.1)octane-2-one;

d. 7-methoxy-2-methoxycarbonyl-8-azabicyclo(3.2.1)octane-2-one;

e. 6-methoxymethoxy-2-methoxycarbonyl-8-azabicyclo(3.2.1)octane-2-one; and f. 7-methoxymethoxy-2-methoxycarbonyl-8-azabicyclo(3.2.1)octane-2-one.

20. The compound of claim 1 selected from the group consisting of:

y. 2β-Carbomethoxy-3-(3,4-dichlorophenyl)-7-methoxymethoxy-8-azabicyclo(3.2.1)octane;

z. 2β-carbomethoxy-3-(3,4-dichlorophenyl)-7-methoxymethoxy-8-azabicyclo(3.2.1)octane;

aa. 2β-Carbomethoxy-3-(3,4-dichlorophenyl)-7-methoxymethoxy-8-azabicyclo(3.2.1)octane;

ab. 2β-carbomethoxy-3-(3,4-dichlorophenyl)-7-methoxymethoxy-8-azabicyclo(3.2.1)octane;

ac. 2β-Carbomethoxy-3-(3,4-dichlorophenyl)-7-methoxy-8-azabicyclo(3.2.1)octane;

ad. 2β-carbomethoxy-3β-(3,4-dichlorophenyl)-7-methoxy-8-azabicyclo(3.2.1)octane;

ae. 2β-Carbomethoxy-3-(fluorophenyl)-7-methoxy-8-azabicyclo(3.2.1)octane; and af. 2β-Carbomethoxy-3β-(fluorophenyl)-7-methoxy-8-azabicyclo(3.2.1)octane.

21. A method for inhibiting 5-hydroxytryptamine reuptake of a monoamine transporter comprising contacting the monoamine transporter with a compound having the structural formula:

I.

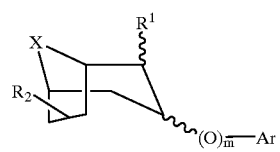

II.

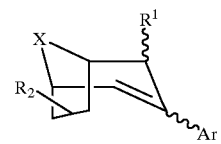

III.

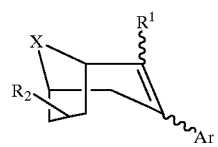

wherein:

$R_1$=COOCH$_3$, COR$_3$, lower alkyl, lower alkenyl, lower alkynyl, CONHR$_4$, or COR$_6$;

$R_2$=is a 6α, 6β, 7α or 7β substituent, which can be selected from OH, OR$_3$, F, Cl, Br, and NHR$_3$;

X=NR$_3$, or NSO$_2$R$_3$;

$R_3$=H, CH$_3$, CH$_3$CH$_2$, CH$_3$(CH$_2$)$_n$ (CH$_2$)$_n$C$_6$H$_4$Y, C$_6$H$_4$Y, CHCH$_2$, lower alkyl, lower alkenyl or lower alkynyl;

Y=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

$R_4$=CH$_3$, CH$_2$CH$_3$, or CH$_2$SO$_2$;

Ar=phenyl-R$_5$, naphthyl-R$_5$, anthracenyl-R$_5$, phenanthrenyl-R$_5$, or diphenylmethoxy-R$_5$;

$R_5$=Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

$R_6$=morpholinyl or piperidinyl;

m=0 or 1; and n=0, 1, 2, 3, 4 or 5;

when X=N, $R_1$ is not COR$_6$.

22. The method of claim 21, wherein the monoamine transporter is selected from the group consisting of a dopamine transporter, a serotonin transporter and a norepinephrine transporter.

23. The method of claim 21, wherein the compound is selected from the group consisting of:

ah. 6-hydroxy-2-methoxycarbonyl-8-azabicyclo(3.2.1)octane-2-one;

ah. 7-hydroxy-2-methoxycarbonyl-8-azabicyclo(3.2.1)octane-2-one;

ai. 6-methoxy-2-methoxycarbonyl-8-azabicyclo(3.2.1)octane-2-one;

aj. 7-methoxy-2-methoxycarbonyl-8-azabicyclo(3.2.1)octane-2-one;

ak. 6-methoxymethoxy-2-methoxycarbonyl-8-azabicyclo(3.2.1)octane-2-ones;

al. 7-methoxymethoxy-2-methoxycarbonyl-8-azabicyclo(3.2.1)octane-2-ones;

am. 2-Carbomethoxy-3-trifluoromethylsulfonyloxy-7-methoxymethoxy-8-azabicyclo(3.2.1)-2-octene;

an. 2-Carbomethoxy-3-(trifluoromethyl)sulfonyloxy-6-methoxymethoxy-8-azabicyclo(3.2.1)-2-octene;

ao. 2-Carbomethoxy-3-trifluoromethylsulfonyloxy-7-methoxy-8-azabicyclo(3.2.1)-2-octene;
ap. 2-Carbomethoxy-3-(3,4-dichlorophenyl)-7-methoxymethoxy-8-azabicyclo(3.2.1)-2-octene;
aq. 2-Carbomethoxy-3-(4-fluorophenyl)-7-methoxymethoxy-8-azabicyclo(3.2.1)-2-octene;
ar. 2-Carbomethoxy-3-(3,4-dichlorophenyl)-7-methoxy-8-azabicyclo(3.2.1)-2-octene;
as. 2-Carbomethoxy-3-(4-fluorophenyl)-7-methoxy-8-azabicyclo(3.2.1)-2-octene;
at. 2β-Carbomethoxy-3-(3,4-dichlorophenyl)-7-methoxymethoxy-8-azabicyclo(3.2.1)octane;
au. 2β-carbomethoxy-3-(3,4-dichlorophenyl)-7-methoxymethoxy-8-azabicyclo(3.2.1)octane;
av. 2β-Carbomethoxy-3-(3,4-dichlorophenyl)-7-methoxymethoxy-8-azabicyclo(3.2.1)octane;
aw. 2β-carbomethoxy-3-(3,4-dichlorophenyl)-7-methoxymethoxy-8-azabicyclo(3.2.1)octane;
ax. 2β-Carbomethoxy-3-(3,4-dichlorophenyl)-7-methoxy-8-azabicyclo(3.2.1)octane;
ay. 2β-carbomethoxy-3β-(3,4-dichlorophenyl)-7-methoxy-8-azabicyclo(3.2.1)octane;
az. 2β-Carbomethoxy-3-(fluorophenyl)-7-methoxy-8-azabicyclo(3.2.1)octane; and
aaa. 2β-Carbomethoxy-3β-(fluorophenyl)-7-methoxy-8-azabicyclo(3.2.1)octane.

24. The method of claim 21, wherein the compound is selected from the group consisting of:
   i. 2-Carbomethoxy-3-trifluoromethylsulfonyloxy-7-methoxymethoxy-8-azabicyclo(3.2.1)-2-octene;
   j. 2-Carbomethoxy-3-(trifluoromethyl)sulfonyloxy-6-methoxymethoxy-8-axabicyclo(3.2.1)-2-octene;
   k. 2-Carbomethoxy-3-trifluoromethylsulfonyloxy-7-methoxy-8-azabicyclo(3.2.1)-2-octene;
   l. 2-Carbomethoxy-3-(3,4-dichlorophenyl)-7-methoxymethoxy-8-azabicyclo(3.2.1)-2-octene;
   m. 2-Carbomethoxy-3-(4-fluorophenyl)-7-methoxymethoxy-8-azabicyclo(3.2.1)-2-octene;
   n. 2-Carbomethoxy-3-(3,4-dichlorophenyl)-7-methoxy-8-azabicyclo(3.2.1)-2-octene; and
   o. 2-Carbomethoxy-3-(4-fluorophenyl)-7-methoxy-8-azabicyclo(3.2.1)-2-octene.

25. The method of claim 21, wherein the compound is selected from the group consisting of:
   a. 6-hydroxy-2-methoxycarbonyl-8-azabicyclo(3.2.1)octane-2-one;
   b. 7-hydroxy-2-methoxycarbonyl-8-azabicyclo(3.2.1)octane-2-one;
   c. 6-methoxy-2-methoxycarbonyl-8-azabicyclo(3.2.1)octane-2-one;
   d. 7-methoxy-2-methoxycarbonyl-8-azabicyclo(3.2.1)octane-2-one;
   e. 6-methoxymethoxy-2-methoxycarbonyl-8-azabicyclo(3.2.1)octane-2-one; and
   f. 7-methoxymethoxy-2-methoxycarbonyl-8-azabicyclo(3.2.1)octane-2-one.

26. The method of claim 21, wherein the compound is selected from the group consisting of:
   y. 2β-Carbomethoxy-3-(3,4-dichlorophenyl)-7-methoxymethoxy-8-azabicyclo(3.2.1)octane;
   z. 2β-carbomethoxy-3-(3,4-dichlorophenyl)-7-methoxymethoxy-8-azabicyclo(3.2.1)octane;
   aa. 2β-Carbomethoxy-3-(3,4-dichlorophenyl)-7-methoxymethoxy-8-azabicyclo(3.2.1)octane;
   ab. 2β-carbomethoxy-3-(3,4-dichlorophenyl)-7-methoxymethoxy-8-azabicyclo(3.2.1)octane;
   ac. 2β-Carbomethoxy-3-(3,4-dichlorophenyl)-7-methoxy-8-azabicyclo(3.2.1)octane;
   ad. 2β-carbomethoxy-3β-(3,4-dichlorophenyl)-7-methoxy-8-azabicyclo(3.2.1)octane;
   ae. 2β-Carbomethoxy-3-(fluorophenyl)-7-methoxy-8-azabicyclo(3.2.1)octane; and
   af. 2β-Carbomethoxy-3β-(fluorophenyl)-7-methoxy-8-azabicyclo(3.2.1)octane.

27. A method for inhibiting 5-hydroxytryptamine reuptake of a monoamine transporter in a mammal comprising administering to the mammal a 5-hydroxytryptamine reuptake inhibiting amount of a compound having the structural formula:

I.

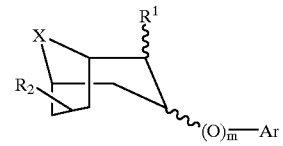

II.

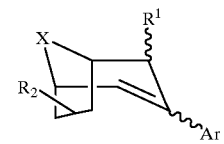

III.

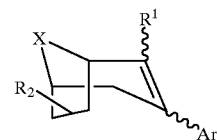

wherein:
   $R_1$=COOCH$_3$, COR$_3$, lower alkyl, lower alkenyl, lower alkynyl, CONHR$_4$, or COR$_6$;
   $R_2$=is a 6α, 6β, 7α or 7β substituent, which can be selected from OH, OR$_3$, F, Cl, Br, and NHR$_3$;
   X=NR$_3$, or NSO$_2$R$_3$;
   $R_3$=H, CH$_3$, CH$_3$CH$_2$, CH$_3$(CH$_2$)$_n$ (CH$_2$)$_n$C$_6$H$_4$Y, C$_6$H$_4$Y, CHCH$_2$, lower alkyl, lower alkenyl or lower alkynyl;
   Y=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;
   $R_4$=CH$_3$, CH$_2$CH$_3$, or CH$_3$SO$_2$;
   Ar=phenyl-R$_5$, naphthyl-R$_5$, anthracenyl-R$_5$, phenanthrenyl-R$_5$, or diphenylmethoxy-R$_5$;
   $R_5$=Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0–6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

$R_6$=morpholinyl or piperidinyl;
m=0 or 1; and
n=0, 1, 2, 3, 4 or 5;
when X=N, $R_1$ is not $COR_6$.

28. The method of claim 27, wherein the compound is selected from the group consisting of:
   ah. 6-hydroxy-2-methoxycarbonyl-8-azabicyclo(3.2.1)octane-2-one;
   ah. 7-hydroxy-2-methoxycarbonyl-8-azabicyclo(3.2.1)octane-2-one;
   ai. 6-methoxy-2-methoxycarbonyl-8-azabicyclo(3.2.1)octane-2-one;
   aj. 7-methoxy-2-methoxycarbonyl-8-azabicyclo-(3.2.1)octane-2-one;
   ak. 6-methoxymethoxy-2-methoxycarbonyl-8-azabicyclo(3.2.1)octane-2-ones;
   al. 7-methoxymethoxy-2-methoxycarbonyl-8-azabicyclo(3.2.1)octane-2-ones;
   am. 2-Carbomethoxy-3-trifluoromethylsulfonyloxy-7-methoxymethoxy-8-azabicyclo(3.2.1)-2-octene;
   an. 2-Carbomethoxy-3-(trifluoromethyl)sulfonyloxy-6-methoxymethoxy-8-azabicyclo(3.2.1)-2-octene;
   ao. 2-Carbomethoxy-3-trifluoromethylsulfonyloxy-7-methoxy-8-azabicyclo(3.2.1)-2-octene;
   ap. 2-Carbomethoxy-3-(3,4-dichlorophenyl)-7-methoxymethoxy-8-azabicyclo(3.2.1)-2-octene;
   aq. 2-Carbomethoxy-3-(4-fluorophenyl)-7-methoxymethoxy-8-azabicyclo(3.2.1)-2-octene;
   ar. 2-Carbomethoxy-3-(3,4-dichlorophenyl)-7-methoxy-8-azabicyclo(3.2.1)-2-octene;
   as. 2-Carbomethoxy-3-(4-fluorophenyl)-7-methoxy-8-azabicyclo(3.2.1)-2-octene;
   at. 2β-Carbomethoxy-3-(3,4-dichlorophenyl)-7-methoxymethoxy-8-azabicyclo(3.2.1)octane;
   au. 2β-carbomethoxy-3-(3,4-dichlorophenyl)-7-methoxymethoxy-8-azabicyclo(3.2.1)octane;
   av. 2β-Carbomethoxy-3-(3,4-dichlorophenyl)-7-methoxymethoxy-8-azabicyclo(3.2.1)octane;
   aw. 2β-carbomethoxy-3-(3,4-dichlorophenyl)-7-methoxymethoxy-8-azabicyclo(3.2.1)octane;
   ax. 2β-Carbomethoxy-3-(3,4-dichlorophenyl)-7-methoxy-8-azabicyclo(3.2.1)octane;
   ay. 2β-carbomethoxy-3β-(3,4-dichlorophenyl)-7-methoxy-8-azabicyclo(3.2.1)octane;
   az. 2β-Carbomethoxy-3-(fluorophenyl)-7-methoxy-8-azabicyclo(3.2.1)octane; and
   aaa. 2β-Carbomethoxy-3β-(fluorophenyl)-7-methoxy-8-azabicyclo(3.2.1)octane.

29. The method of claim 27, wherein the compound is selected from the group consisting of:
   i. 2-Carbomethoxy-3-trifluoromethylsulfonyloxy-7-methoxymethoxy-8-azabicyclo(3.2.1)-2-octene;
   j. 2-Carbomethoxy-3-(trifluoromethyl)sulfonyloxy-6-methoxymethoxy-8-axabicyclo(3.2.1)-2-octene;
   k. 2-Carbomethoxy-3-trifluoromethylsulfonyloxy-7-methoxy-8-azabicyclo(3.2.1)-2-octene;
   l. 2-Carbomethoxy-3-(3,4-dichlorophenyl)-7-methoxymethoxy-8-azabicyclo(3.2.1)-2-octene;
   m. 2-Carbomethoxy-3-(4-fluorophenyl)-7-methoxymethoxy-8-azabicyclo(3.2.1)-2-octene;
   n. 2-Carbomethoxy-3-(3,4-dichlorophenyl)-7-methoxy-8-azabicyclo(3.2.1)-2-octene; and
   o. 2-Carbomethoxy-3-(4-fluorophenyl)-7-methoxy-8-azabicyclo(3.2.1)-2-octene.

30. The method of claim 27, wherein the compound is selected from the group consisting of:
   a. 6-hydroxy-2-methoxycarbonyl-8-azabicyclo(3.2.1)octane-2-one;
   b. 7-hydroxy-2-methoxycarbonyl-8-azabicyclo(3.2.1)octane-2-one;
   c. 6-methoxy-2-methoxycarbonyl-8-azabicyclo(3.2.1)octane-2-one;
   d. 7-methoxy-2-methoxycarbonyl-8-azabicyclo(3.2.1)octane-2-one;
   e. 6-methoxymethoxy-2-methoxycarbonyl-8-azabicyclo(3.2.1)octane-2-one; and
   f. 7-methoxymethoxy-2-methoxycarbonyl-8-azabicyclo(3.2.1)octane-2-one.

31. The method of claim 27, wherein the compound is selected from the group consisting of:
   y. 2β-Carbomethoxy-3-(3,4-dichlorophenyl)-7-methoxymethoxy-8-azabicyclo(3.2.1)octane;
   z. 2β-carbomethoxy-3-(3,4-dichlorophenyl)-7-methoxymethoxy-8-azabicyclo(3.2.1)octane;
   aa. 2β-Carbomethoxy-3-(3,4-dichlorophenyl)-7-methoxymethoxy-8-azabicyclo(3.2.1)octane;
   ab. 2β-carbomethoxy-3-(3,4-dichlorophenyl)-7-methoxymethoxy-8-azabicyclo(3.2.1)octane;
   ac. 2β-Carbomethoxy-3-(3,4-dichlorophenyl)-7-methoxy-8-azabicyclo(3.2.1)octane;
   ad. 2β-carbomethoxy-3β-(3,4-dichlorophenyl)-7-methoxy-8-azabicyclo(3.2.1)octane;
   ae. 2β-Carbomethoxy-3-(fluorophenyl)-7-methoxy-8-azabicyclo(3.2.1)octane; and
   af. 2β-Carbomethoxy-3β-(fluorophenyl)-7-methoxy-8-azabicyclo(3.2.1)octane.

32. A method for inhibiting dopamine reuptake of a dopamine transporter in a mammal comprising administering to the mammal a dopamine reuptake inhibiting amount of a compound having the structural formula:

I.

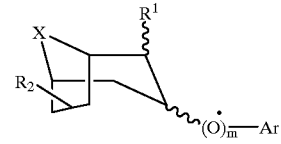

II.

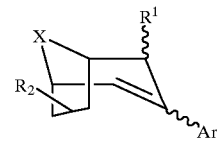

III.

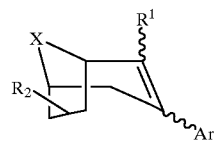

wherein:
   $R_1$=COOCH$_3$, COR$_3$, lower alkyl, lower alkenyl, lower alkynyl, CONHR$_4$, or COR$_6$;

R$_2$=is a 6α, 6β, 7α or 7β substituent, which can be selected from OH, OR$_3$, F, Cl, Br, and NHR$_3$;

X=NR$_3$, or NSO$_2$R$_3$,

R$_3$=H, CH$_3$, CH$_3$CH$_2$, CH$_3$(CH$_2$)$_n$ (CH$_2$)$_n$C$_6$H$_4$Y, C$_6$H$_4$Y, CHCH$_2$, lower alkyl, lower alkenyl or lower alkynyl;

Y=H, Br, Cl, I, F, OH, OCH$_3$, CF$_3$, NO$_2$, NH$_2$, CN, NHCOCH$_3$, N(CH$_3$)$_2$, (CH$_2$)$_n$CH$_3$, COCH$_3$, or C(CH$_3$)$_3$;

R$_4$=CH$_3$, CH$_2$CH$_3$, or CH$_3$SO$_2$;

Ar=phenyl-R$_5$, naphthyl-R$_5$, anthracenyl-R$_5$, phenanthrenyl-R$_5$, or diphenylmethoxy-R$_5$;

R$_5$=Br, Cl, I, F, OH, OCH$_3$, CF$_3$, NO$_2$, NH$_2$, CN, NHCOCH$_3$, N(CH$_3$)$_2$, (CH$_2$)nCH$_3$, COCH$_3$, C(CH$_3$)$_3$ where n=0-6, 4-F, 4-Cl, 4-I, 2-F, 2-Cl, 2-I, 3-F, 3-Cl, 3-I, 3,4-diCl, 3,4-diOH, 3,4-diOAc, 3,4-diOCH$_3$, 3-OH-4-Cl, 3-OH-4-F, 3-Cl-4-OH, 3-F-4-OH, lower alkyl, lower alkoxy, lower alkenyl, lower alkynyl, CO(lower alkyl), or CO(lower alkoxy);

R$_6$=morpholinyl or piperidinyl;

m=0 or 1; and n=0, 1, 2, 3, 4 or 5;

when X=N, R$_1$ is not COR$_6$.

33. The method of claim 32, wherein the compound is selected from the group consisting of:
 ah. 6-hydroxy-2-methoxycarbonyl-8-azabicyclo(3.2.1)octane-2-one;
 ah. 7-hydroxy-2-methoxycarbonyl-8-azabicyclo(3.2.1)octane-2-one;
 ai. 6-methoxy-2-methoxycarbonyl-8-azabicyclo(3.2.1)octane-2-one;
 aj. 7-methoxy-2-methoxycarbonyl-8-azabicyclo(3.2.1)octane-2-one;
 ak. 6-methoxymethoxy-2-methoxycarbonyl-8-azabicyclo(3.2.1)octane-2-ones;
 al. 7-methoxymethoxy-2-methoxycarbonyl-8-azabicyclo(3.2.1)octane-2-ones;
 am. 2-Carbomethoxy-3-trifluoromethylsulfonyloxy-7-methoxymethoxy-8-azabicyclo(3.2.1)-2-octene;
 an. 2-Carbomethoxy-3-(trifluoromethyl)sulfonyloxy-6-methoxymethoxy-8-azabicyclo(3.2.1)-2-octene;
 ao. 2-Carbomethoxy-3-trifluoromethylsulfonyloxy-7-methoxy-8-azabicyclo(3.2.1)-2-octene;
 ap. 2-Carbomethoxy-3-(3,4-dichlorophenyl)-7-methoxymethoxy-8-azabicyclo(3.2.1)-2-octene;
 aq. 2-Carbomethoxy-3-(4-fluorophenyl)-7-methoxymethoxy-8-azabicyclo(3.2.1)-2-octene;
 ar. 2-Carbomethoxy-3-(3,4-dichlorophenyl)-7-methoxy-8-azabicyclo(3.2.1)-2-octene;
 as. 2-Carbomethoxy-3-(4-fluorophenyl)-7-methoxy-8-azabicyclo(3.2.1)-2-octene;
 at. 2β-Carbomethoxy-3-(3,4-dichlorophenyl)-7-methoxymethoxy-8-azabicyclo(3.2.1)octane;
 au. 2β-carbomethoxy-3-(3,4-dichlorophenyl)-7-methoxymethoxy-8-azabicyclo(3.2.1)octane;
 av. 2β-Carbomethoxy-3-(3,4-dichlorophenyl)-7-methoxymethoxy-8-azabicyclo(3.2.1)octane;
 aw. 2β-carbomethoxy-3-(3,4-dichlorophenyl)-7-methoxymethoxy-8-azabicyclo(3.2.1)octane;
 ax. 2β-Carbomethoxy-3-(3,4-dichlorophenyl)-7-methoxy-8-azabicyclo(3.2.1)octane;
 ay. 2β-carbomethoxy-3β-(3,4-dichlorophenyl)-7-methoxy-8-azabicyclo(3.2.1)octane;
 az. 2β-Carbomethoxy-3-(fluorophenyl)-7-methoxy-8-azabicyclo(3.2.1)octane; and
 aaa. 2β-Carbomethoxy-3β-(fluorophenyl)-7-methoxy-8-azabicyclo(3.2.1)octane.

34. The method of claim 32, wherein the compound is selected from the group consisting of:
 i. 2-Carbomethoxy-3-trifluoromethylsulfonyloxy-7-methoxymethoxy-8-azabicyclo(3.2.1)-2-octene;
 j. 2-Carbomethoxy-3-(trifluoromethyl)sulfonyloxy-6-methoxymethoxy-8-axabicyclo(3.2.1)-2-octene;
 k. 2-Carbomethoxy-3-trifluoromethylsulfonyloxy-7-methoxy-8-azabicyclo(3.2.1)-2-octene;
 l. 2-Carbomethoxy-3-(3,4-dichlorophenyl)-7-methoxymethoxy-8-azabicyclo(3.2.1)-2-octene;
 m. 2-Carbomethoxy-3-(4-fluorophenyl)-7-methoxymethoxy-8-azabicyclo(3.2.1)-2-octene;
 n. 2-Carbomethoxy-3-(3,4-dichlorophenyl)-7-methoxy-8-azabicyclo(3.2.1)-2-octene; and
 o. 2-Carbomethoxy-3-(4-fluorophenyl)-7-methoxy-8-azabicyclo(3.2.1)-2-octene.

35. The method of claim 32, wherein the compound is selected from the group consisting of:
 a. 6-hydroxy-2-methoxycarbonyl-8-azabicyclo(3.2.1)octane-2-one;
 b. 7-hydroxy-2-methoxycarbonyl-8-azabicyclo(3.2.1)octane-2-one;
 c. 6-methoxy-2-methoxycarbonyl-8-azabicyclo(3.2.1)octane-2-one;
 d. 7-methoxy-2-methoxycarbonyl-8-azabicyclo(3.2.1)octane-2-one;
 e. 6-methoxymethoxy-2-methoxycarbonyl-8-azabicyclo(3.2.1)octane-2-one; and
 f. 7-methoxymethoxy-2-methoxycarbonyl-8-azabicyclo(3.2.1)octane-2-one.

36. The method of claim 32, wherein the compound is selected from the group consisting of:
 y. 2β-Carbomethoxy-3-(3,4-dichlorophenyl)-7-methoxymethoxy-8-azabicyclo(3.2.1)octane;
 z. 2β-carbomethoxy-3-(3,4-dichlorophenyl)-7-methoxymethoxy-8-azabicyclo(3.2.1)octane;
 aa. 2β-Carbomethoxy-3-(3,4-dichlorophenyl)-7-methoxymethoxy-8-azabicyclo(3.2.1)octane;
 ab. 2β-carbomethoxy-3-(3,4-dichlorophenyl)-7-methoxymethoxy-8-azabicyclo(3.2.1)octane;
 ac. 2β-Carbomethoxy-3-(3,4-dichlorophenyl)-7-methoxy-8-azabicyclo(3.2.1)octane;
 ad. 2β-carbomethoxy-3β-(3,4-dichlorophenyl)-7-methoxy-8-azabicyclo(3.2.1)octane;
 ae. 2β-Carbomethoxy-3-(fluorophenyl)-7-methoxy-8-azabicyclo(3.2.1)octane; and
 af. 2β-carbomethoxy-3β-(fluorophenyl)-7-methoxy-8-azabicyclo(3.2.1)octane.

* * * * *